(12) United States Patent
Risk, Jr. et al.

(10) Patent No.: US 6,764,462 B2
(45) Date of Patent: Jul. 20, 2004

(54) WOUND TREATMENT APPARATUS

(75) Inventors: James R. Risk, Jr., Fountaintown, IN (US); Robert Petrosenko, Batesville, IN (US)

(73) Assignee: Hill-Rom Services Inc., Batesville, IN (US)

(*) Notice: Subject to any disclaimer, the term of this patent is extended or adjusted under 35 U.S.C. 154(b) by 16 days.

(21) Appl. No.: 10/159,583

(22) Filed: May 31, 2002

(65) Prior Publication Data

US 2002/0198504 A1 Dec. 26, 2002

Related U.S. Application Data

(63) Continuation-in-part of application No. 09/725,666, filed on Nov. 29, 2000.

(51) Int. Cl.⁷ .......................... A61M 31/00; A61M 1/00; G01N 21/00
(52) U.S. Cl. ........................... 604/67; 604/119; 73/1.06
(58) Field of Search ..................... 604/65, 67, 118–120, 604/305, 313, 315, 541, 543; 73/1.06, 1.35

(56) References Cited

U.S. PATENT DOCUMENTS

| | | | |
|---|---|---|---|
| 3,831,588 A | * | 8/1974 | Rindner ...................... 600/488 |
| 4,930,997 A | | 6/1990 | Bennett |
| 5,045,777 A | | 9/1991 | Itagaki |
| 5,380,280 A | * | 1/1995 | Peterson ...................... 604/65 |
| 5,484,428 A | | 1/1996 | Drainville et al. |
| 5,624,418 A | | 4/1997 | Shepard |
| 5,669,892 A | | 9/1997 | Keogh et al. |
| 5,672,152 A | | 9/1997 | Mason et al. |
| 5,741,237 A | | 4/1998 | Walker |
| 6,017,493 A | | 1/2000 | Cambron et al. |
| 6,039,724 A | | 3/2000 | Seifert et al. |
| 6,056,730 A | | 5/2000 | Greter |
| 6,093,230 A | | 7/2000 | Johnson, III et al. |
| 6,244,311 B1 | | 6/2001 | Hand et al. |
| 6,691,047 B1 | * | 2/2004 | Fredericks ................... 702/47 |

FOREIGN PATENT DOCUMENTS

| | | |
|---|---|---|
| EP | 0 853 950 A1 | 7/1998 |
| GB | 2 342 584 A | 4/2000 |
| GB | 2 344 531 A | 6/2000 |
| WO | WO 96/05873 | 2/1996 |
| WO | WO 97/18007 | 5/1997 |
| WO | WO 00/07653 | 2/2000 |
| WO | WO 00/21586 | 4/2000 |
| WO | WO 00/61206 | 10/2000 |
| WO | WO 01/34223 | 5/2001 |

OTHER PUBLICATIONS

KCI V.A.C. ® ATS Product Brochure (7 pages, published in 2002, before May 31, 2002).

* cited by examiner

Primary Examiner—John J. Calvert
Assistant Examiner—Linh Truong
(74) Attorney, Agent, or Firm—Barnes & Thornburg

(57) ABSTRACT

A wound treatment apparatus is disclosed to provide vacuum therapy to a wound associated with a patient. The wound treatment apparatus comprises a control unit comprising an alarm and a display displaying an alarm log providing information associated with each activation of the alarm. The display also displays information to instruct a user how to operate the wound treatment apparatus. A method of calibrating the control unit is disclosed.

17 Claims, 28 Drawing Sheets

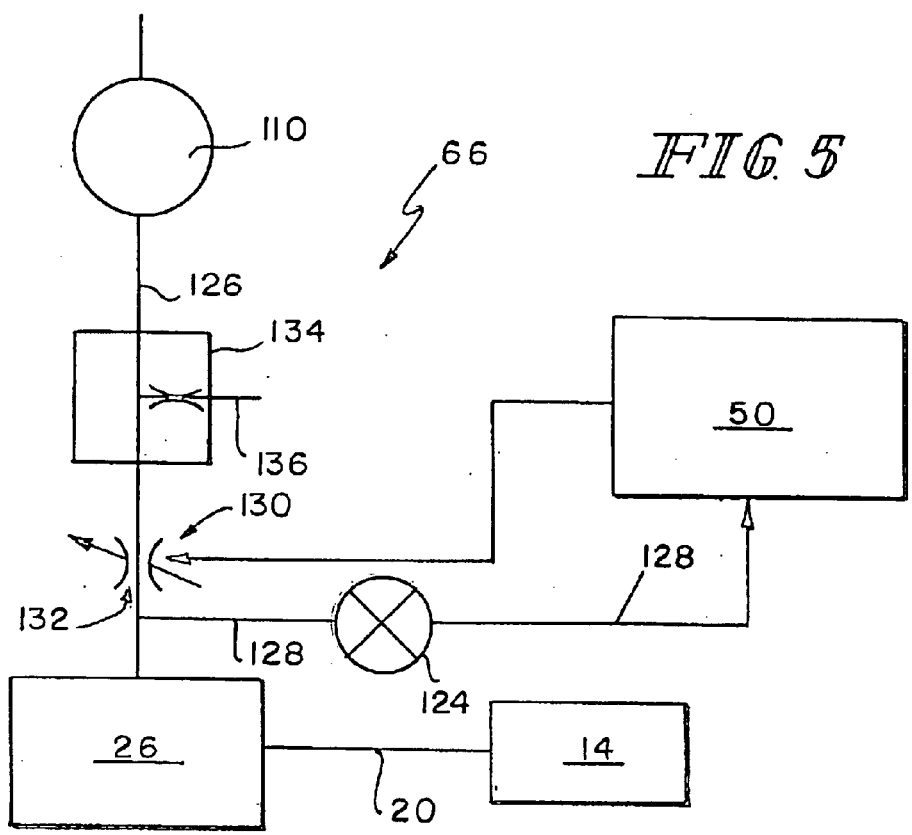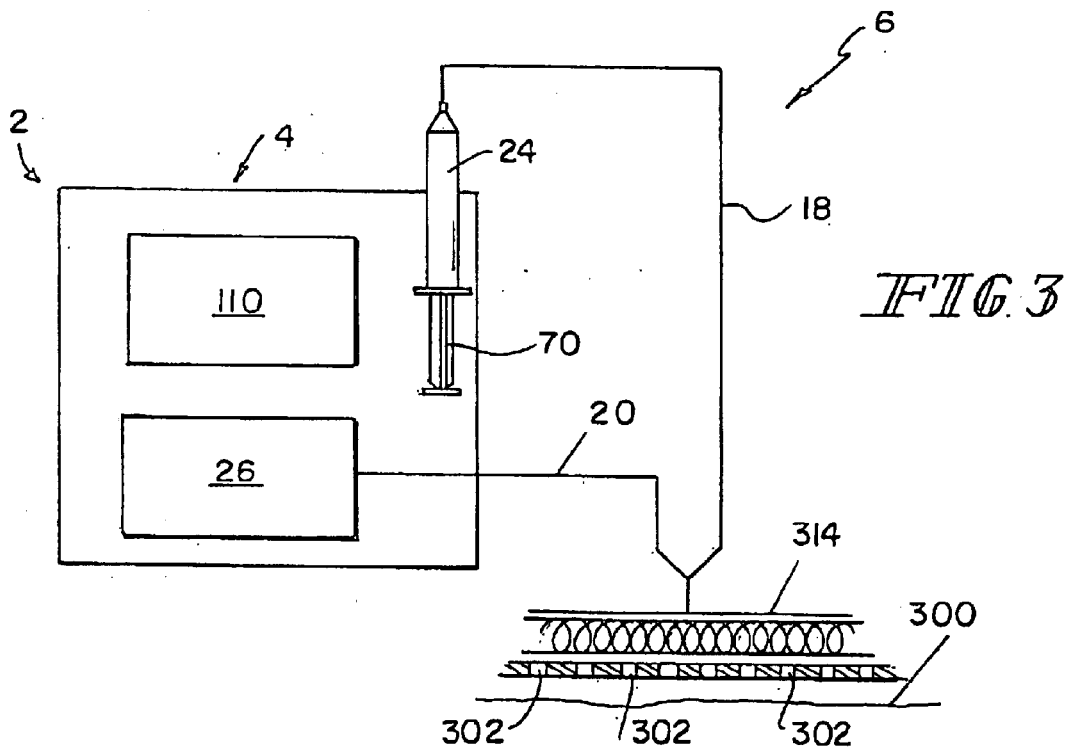

ically treat patients having surface wounds of varying size,
WOUND TREATMENT APPARATUS This disclosure is a continuation-in-part of U.S. application Ser. No. 09/725,666, which was filed Nov. 29, 2000 and which is hereby incorporated by reference herein.

BACKGROUND AND SUMMARY

The present disclosure relates to wound treatment apparatus for use with vacuum bandages of the type that dispenses fluid to a wound and draws fluid away from the wound.

Medical professionals, such as nurses and doctors, routinely treat patients having surface wounds of varying size, shape, and severity. It is known that controlling the topical atmosphere adjacent a wound can enhance the healing process. For example, by applying medicinal agents or even water over a wound, dirt and bacteria are either killed or washed away, thereby promoting healing. In addition, applying a negative pressure or vacuum to a wound draws out exudate, which might contain dirt and bacteria, from the wound to further promote healing.

Conventional treatment of a surface wound involves placement of a packing or dressing material, such as cotton, gauze, or other bandage-like material directly in contact with the patient's wound. Often there is a need to change the dressing material frequently because it becomes saturated with exudate discharged from the wound. Some dressings include an apparatus attached thereto for applying a vacuum through the bandage to the wound to draw exudate and promote healing.

According to the present disclosure, a method for calibrating a control unit adapted to provide a negative pressure through a vacuum wound bandage associated with a wound of a patient comprises positioning a first pressure sensor in communication with the control unit. The method comprises correlating a first output of a second pressure sensor of the control unit to a first calibration pressure when the first pressure sensor senses the first calibration pressure and correlating a second output of the second pressure sensor to a second calibration pressure when the second pressure sensor senses the second calibration pressure.

According to another aspect of the disclosure, the control unit comprises an alarm and a display. The display displays an alarm log providing information associated with each activation of the alarm.

According to another aspect of the disclosure, a wound treatment apparatus is adapted for use with the vacuum wound bandage associated with the wound of the patient to provide negative pressure through the vacuum wound bandage to the wound. The wound treatment apparatus comprises a user input control and an electronic display displaying information comprising a graphical representation of the user input control and text associated with the graphical representation to instruct a user when to operate the user input control. In some embodiments, the electronic display displays information that instructs the user how to operate the wound treatment apparatus during normal operation of the wound treatment apparatus and the information is executable to operate the wound treatment apparatus when the display is displaying the information.

Additional features and advantages of the apparatus will become apparent to those skilled in the art upon consideration of the following detailed descriptions exemplifying the best mode of carrying out the apparatus as presently perceived.

BRIEF DESCRIPTION OF THE DRAWINGS

The illustrative apparatus will be described hereinafter with reference to the attached drawings, which are given as non-limiting examples only, in which:

FIG. 3 is a schematic diagram of the wound treatment apparatus of FIG. 1;

FIG. 5 is a schematic block diagram of the vacuum evacuating subsystem of the wound treatment apparatus of FIG. 1;

Corresponding reference characters indicate corresponding parts throughout the several views. The exemplification set out herein illustrates several embodiments of the apparatus, and such exemplification is not to be construed as limiting the scope of this disclosure in any manner.

DETAILED DESCRIPTION OF DRAWINGS

Figure 1:
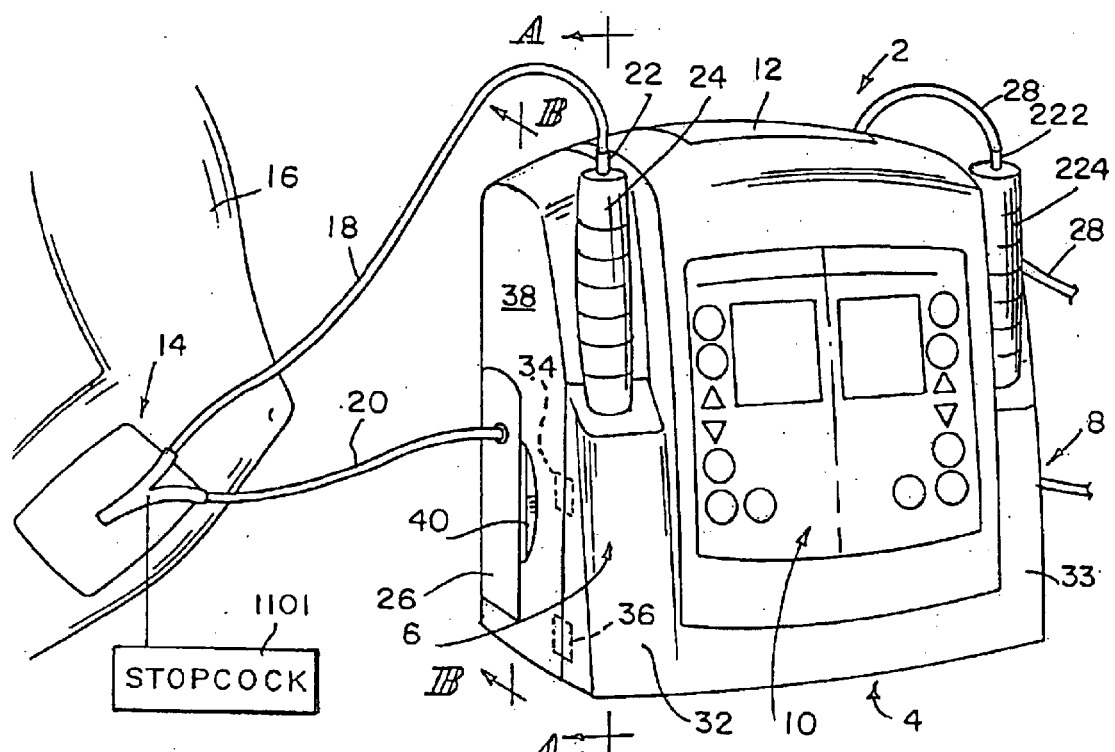
FIG. 1 is a perspective view of a wound treatment apparatus coupled to a bandage attached to a patient.

An embodiment of wound treatment apparatus 2 is shown in FIG. 1. Wound treatment apparatus 2 comprises a central unit housing 4, having wound treatment systems 6, 8 appended to each side of housing 4. A user interface 10 is shown positioned between each treatment system 6, 8. Central unit housing 4 is configured to be a portable unit allowing a user, such as a caregiver, to move housing 4 to wherever the patient is located and to close proximity to the wound or wounds. Housing 4 is shown having a handle portion 12 to assist the caregiver in moving housing 4. FIG. 1 also shows wound treatment system 6 coupled to a bandage 14 attached to a patient's leg 16. Dispensing and evacuating tubes 18, 20 are coupled to both bandage 14 and system 6. Specifically, dispensing tube 18 is coupled to a luer-lok port 22 extending from syringe 24. Syringe 24 is filled with a fluid, typically saline, that empties through tube 18 and into bandage 14, and ultimately onto a wound 300 positioned under bandage 14. (See also FIG. 9.) After contacting wound 300, the fluid and exudate from wound 300 are drawn from bandage 14 through evacuating tube 20 and into a waste canister 26 where it is collected. It is contemplated that the canister 26 can be discarded when filled and replaced with a new canister 26.

Apparatus 2 comprises a second system 8 on the opposite side of housing 4 from system 6. This configuration allows two wounds to be treated simultaneously with separate bandages, yet, under the control of a single housing 4. Second bandage 15, as part of system 8, is coupled to dispensing and evacuating tubes 28, 30, respectively, to perform the same functions as described for system 6. (See FIG. 2.) User interface 10 is provided to allow the caregiver to control either or both systems 6, 8, to dispense fluid from either or both syringes 24, 224, and to evacuate from either or both bandages 14, 15. It is contemplated that each wound treatment system 6, 8 will work independent of each other, thus, allowing the caregiver flexibility to apply an appropriate and, yet, possibly different level of treatment to each wound.

The arrangement of systems 6, 8 relative to user interface 10 on housing 4 allows convenient interaction between systems 6, 8 and the caregiver. For example, syringes 24, 224 are conveniently positioned on opposite sides of user interface 10. Each syringe is partially covered by doors 32, 33 on the front of housing 4. Each door 32, 33 swings outwardly about hinges 34, 36, allowing syringes 24, 224 to be removed and replaced. Similarly, waste canisters 26, 27 are each positioned in a cavity 9 provided on each side of housing 4. (See FIG. 7.) Each canister 26, 27 includes a grip portion 40 for convenient removal and replacement. Canisters 26, 27 are illustratively secured into each cavity by a friction fit. (See FIG. 6.) It is appreciated, however, that syringes 24, 224 can be secured to other locations on housing 4.

The portability of apparatus 2 allows a caregiver to position it near the patient in preparation for treatment wherever the patient is located. To prepare apparatus 2 for treatment, the caregiver secures syringes 24, 224, which contain fluid, to apparatus 2 in a manner described in greater detail below. The caregiver then couples tube 18 to port 22 and bandage 14, and tube 20 to bandage 14 and waste canister 26, for treatment of one wound. The caregiver then couples tube 28 to port 222 and bandage 15, and tube 21 to bandage 15 and waste canister 27, for treatment of a second wound. (See also FIG. 2.) The caregiver, through the use of user interface 10 can treat the patient by selectively irrigating the wounds with fluid and drawing exudate and the fluid from the wounds.

Figure 2:
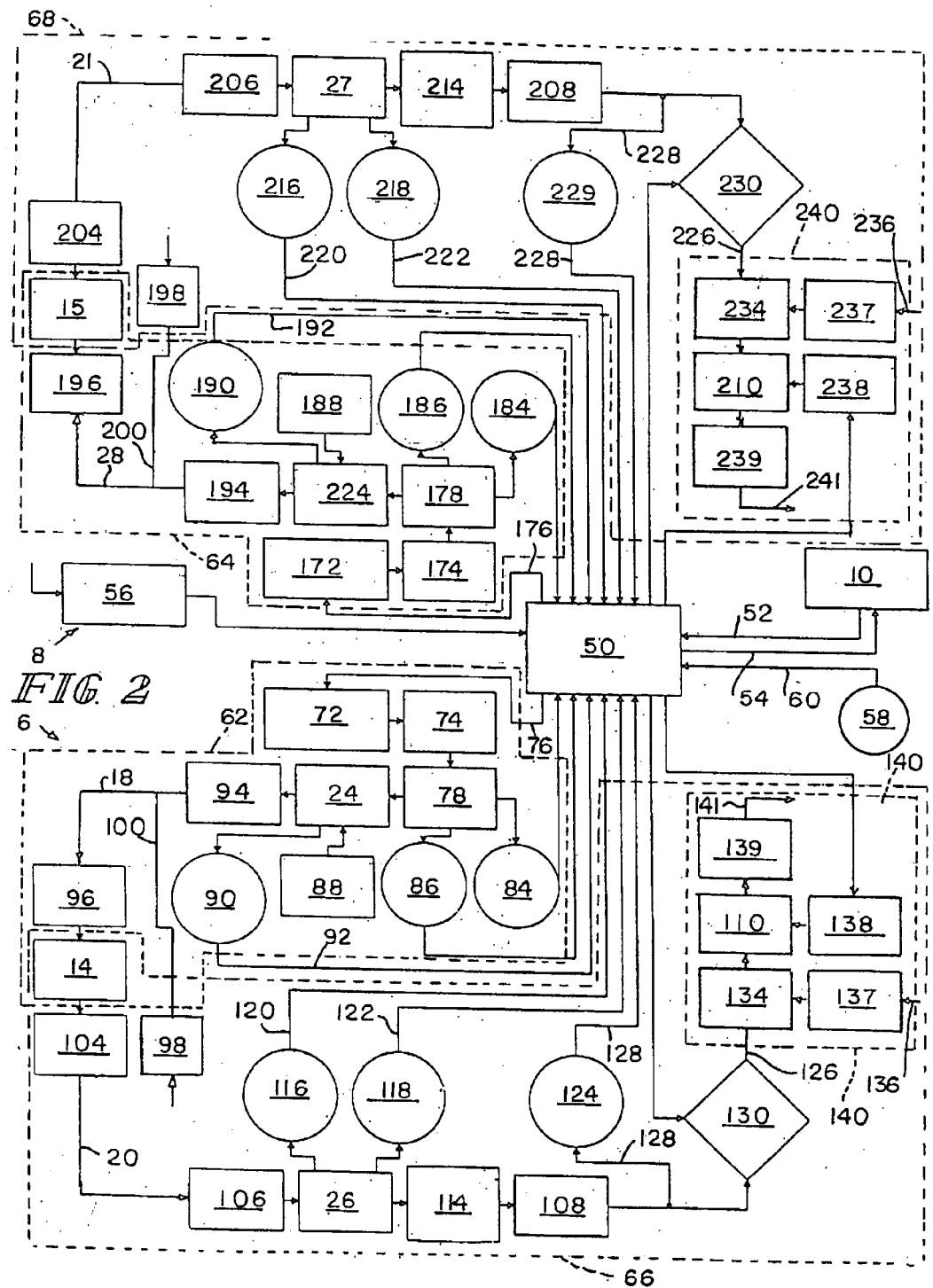
FIG. 2 is a block diagram of the wound treatment apparatus of FIG. 1.

A diagram depicting how wound apparatus 2 operates is shown in FIG. 2. A controller 50 is provided in housing 4 and is an electronic control unit that controls apparatus 2. Controller 50 receives user input from and provides feedback to user interface 10 through lines 52, 54, respectively. It is contemplated that controller 50 will process information from both systems 6, 8, and provide appropriate and independent input to each system. Controller 50 also monitors the status of all various sensors, and provides input for the valves and motors, as discussed in further detail herein. Illustratively, user interface 10 is composed of a conventional graphic liquid crystal display (LCD) and a membrane switch panel.

A power supply 56 provides power to controller 50 and all the attendant systems in housing 4. Power supply 56 can be a conventional external wall socket supply (not shown), or be a battery pack supply (also not shown), or even be variations of both (e.g., a wall socket supply with a battery pack supply). Illustratively, power supply 56 is a medical grade power supply providing an output of about 65 watts and a voltage of about 12VDC. It is contemplated that the power supply can be configured for 120V/60 Hz or 220–240V/50 Hz depending on whether housing 4 is used in America or Europe. Illustratively, the battery power provides the device with power to operate for about 60 minutes without connection to an external power source. It is further contemplated that the batteries can be rechargeable, and store energy when the device is connected to an external wall socket.

An attitude sensor 58 is provided in communication with controller 50 through line 60. Attitude sensor 58 is, illustratively, a tilt switch which provides feedback to controller 50. If the switch is, illustratively, in the closed position, controller 50 will continue to operate, but if the switch opens, controller will shut systems 6, 8 down. For example, sensor 58 disables systems 6, 8 if housing 4 tilts at or greater than a predetermined amount, such as 45° from vertical in any direction.

It is contemplated that controller 50, user interface 10, power supply 56, and attitude sensor 58 are all common to and all operate with both systems 6, 8. Each system 6, 8 further comprises fluid dispensing and vacuum evacuating subsystems 62, 64 and 66, 68. Fluid dispensing sub-system 62 comprises a syringe 24 having a plunger 70. (See also FIG. 4.) Syringe 24 is, illustratively, a standard 60-ml medical syringe utilizing a luer-lok port 22. Plunger 70 is a conventional plunger that extends into syringe 24 to dispense fluid through luer-lok port 22. A syringe drive motor 72 is, illustratively, a 12VDC brushless electric motor or stepper motor configured to provide rotational energy to a syringe drive 74. (See FIG. 4.) When a signal is sent from controller 50 along line 76 to syringe drive motor 72, motor 22 applies torque and angular velocity to syringe drive 74 which is, illustratively, a power screw 322. (See also FIG. 4.) Power screw 322 translates rotational movement of the syringe drive motor 72 into translational movement. The drive has a guide 80 to limit a plunger interface 78 to motion along one axis. In the illustrated embodiment, syringe drive 72 provides about 5.25 inches (13.3 cm) of travel of plunger interface 78, indicated by reference numeral 82, to evacuate the fluid contained in syringe 24. (See also FIG. 4.) Furthermore, syringe drive motor 72 and syringe drive 74, as a system, provide about 27 pounds of linear force at a velocity of 1.45 inches (3.7 cm) per second to the plunger interface 78. The resulting force created by the fluid exiting syringe 24 creates, illustratively, 4-PSIG to 6-PSIG positive pressure at wound 300.

A syringe home sensor 84 receives information from plunger interface 78, and provides feedback to controller 50 when syringe capture mechanism 88 reaches its home position 79. A syringe full travel sensor 86 determines when syringe 24 is fully evacuated by sensing when plunger interface 78 has reached full travel. After sensor 86 has been activated, controller 50 resets plunger interface 78 to home position 79 once syringe 24 is removed.

Syringe capture mechanism 88 holds syringe 24 in place when the caregiver places syringe 24 in apparatus 2. (See also FIG. 4.) Capture mechanism 88 is also configured to allow the caregiver to release syringe 24 from apparatus 2 when it is empty. Capture mechanism 88 further includes a syringe sensor 90 that provides feedback to controller 50 through line 92 when syringe 24 is properly held in capture mechanism 88. Controller 50 prevents system 6 from operating if sensor 90 does not detect syringe 50 being properly held in capture mechanism 88.

Connectors 94, 96 are provided at opposed ends of dispensing tube 18. Either one or both connectors 94, 96, when closed, block flow from syringe 24 to bandage 14. Such connectors 94, 96 allow the patient to be disconnected from apparatus 2 without having to remove bandage 14 or even shut apparatus 2 down.

A manual port 98 is also attached to dispensing tube 18 by an auxiliary tube 100. Port 98 permits the caregiver to attach a dispensing container to the system to manually dispense fluid into bandage 14. It is appreciated, however, that port 98 is configured to be closed while no syringe is attached to maintain a closed system.

The syringe and drive are illustrated as one approach for providing a fluid source and a drive for irrigating a wound bed. It will be appreciated that containers other than syringes may be operated by a drive to expel irrigation fluid toward a wound surface. For example, any type of container of fluid may be squeezed or reduced in volume by a drive mechanism to expel fluid. Also, as discussed in connection with FIG. 8, a container may be held at an elevated position to provide head pressure for irrigation fluid.

Connectors 104, 106, similar to connectors 94, 96, are provided at opposed ends of evacuating tube 20. Either one or both connectors 104, 106, when closed, block flow from bandage 14 to waste canister 26. Such connectors 104, 106 also allow the patient to be disconnected from apparatus 2 without having to remove bandage 14 or having to shut down apparatus 2.

Waste canister sensors 116, 118 are engaged when waste container 26 is properly seated in apparatus 2. This prevents apparatus 2 from operating without canister 26 seated properly in apparatus 2. As depicted in FIG. 2, both sensors 116, 118 provide feedback to controller 50 through lines 120, 122, confirming to the caregiver that canister 26 is seated properly in apparatus 2.

In the illustrated embodiment, waste canister 26 is a disposable unit that "snaps into" side portion 38 of housing 4. (See also FIGS. 1 and 6.) Illustratively, canister 26 includes a window (not shown) to allow monitoring of the fluids. Illustratively, the fluid capacity of canister 26 is about 500-ml.

The illustrated embodiment of waste canister 26 further includes a hydrophobic filter 108 that is in communication with both evacuating tube 20 and vacuum pump 110. (See also FIG. 6.) Such filter 108 is configured to allow air, but not liquid, to pass. Accordingly, as fluid is drawn into canister 26, fluid is deposited into waste canister 26 while the vacuum continues through filter 108 and pump 110. Illustratively, filter 108 is a 1.0-micron hydrophobic filter fixed into rear wall 407 of canister 26. (See FIG. 6.) Hydrophobic filter 108 also serves as a canister full mechanism 114 or valve that shuts off the vacuum supply to the canister 26 when the fluid level exceeds the "full" level 420. Because hydrophobic filter 108 prevents fluid from passing, once fluid covers filter 108, vacuum is prevented from passing as well. The absence of any vacuum in the system will cause the system to shut down.

Vacuum pump 110 creates the negative pressure that is present through canister 26. For monitoring and controlling such negative pressure, the vacuum is present through several devices, including a vacuum pressure transducer 124. Transducer 124 is coupled to line 128, extending from canister 26. (See FIG. 5.) Transducer 124 measures the negative pressure that is present through canister 26. Transducer 124 then provides feedback to controller 50 through line 128. Controller 50 monitors the negative pressure by comparing the measured value from transducer 124 with the caregiver-defined value entered into controller 50 through user interface 10.

A proportional valve 130 is connected to line 126, through which the negative pressure is present, and which comprises a flow orifice 132. (See also FIG. 5.) Flow orifice 132 selectively dilates or constricts, thereby controlling the negative pressure level through sub-system 66. Specifically, controller 50 provides a signal input to proportional valve 130 based on the level of the vacuum pressure determined from feedback of transducer 124 and comparing that level to the caregiver-defined level. Orifice 132 then dilates or constricts, as necessary, to produce the appropriate level of negative pressure. Illustratively, proportional valve 130 is fully constricted or closed when receiving no signal from controller 50, and dilates or opens to allow an illustrative maximum of two liters per minute at 250-mmHg (4.83-PSIG) vacuum when the proper signal from controller 50 is applied.

A vacuum regulator 134 is provided in line 126 between proportional valve 130 and pump 110 as a mechanical limit control for pump 110. Regulator 134 mechanically establishes a maximum level of negative pressure that is present in the system. Thus, vacuum pump 110 will not physically be able to draw a vacuum from bandage 14 beyond the maximum pressure. Illustratively, such maximum negative pressure or vacuum is 250-mmHg (4.83-PSIG). In addition, when proportional valve 130, pursuant to a signal from controller 50, creates a negative pressure less than the maximum negative pressure level, a port 136, coupled to regulator 134, opens so that pump 110 can draw more air to maintain a sufficient flow through pump 110, to prevent it from becoming damaged. A first air filter 137 is illustratively associated with port 136, between port 136 and pump 110, to filter particulates from the air prior to reaching pump 110. Illustratively, filter 137 is constructed of glass microfibers with a filtration rating of 25 microns. A second filter 139 is associated with pump 110 and an outlet 141. Filter 139 serves as an exhaust muffler for the air evacuated from pump 110.

Vacuum pump 110 is, illustratively, a diaphragm-type compressor that flows about two liters per minute at 250-mmHg (4.83-PSIG) vacuum. Illustratively, vacuum pump 110 is mounted on the end of a single 12VDC brushless motor 138 to drive the pump. It is appreciated, however, that pump 110 can be of any other configuration, and mounted in any manner, so long as it draws a desired negative pressure through system 6. It is also contemplated that a vacuum pump external to the housing 4 may be a part of the control system. For example, most medical facilities have vacuum ports near where patients are treated, each of which is served by a system vacuum (suction) pump. It is contemplated, therefore, that the pump 110 in the housing 4 may be an appropriate fitting which is, in turn, connected to a facility vacuum pump to provide a vacuum source to the control system.

It is contemplated that port 136, filters 137, 139, electric motor 138, vacuum pump 110, and vacuum regulator 134 are all housed in a sound chamber 140. Illustratively, the interior of sound chamber 140 is lined with a damping foil like the 3M Company's damping foil number 2552, for example. Sound chamber 140 dampens vibration energy produced by these components, as well as assists in dissipating heat they generated.

As previously indicated, it is contemplated that controller 50, user interface 10, power supply 56, and attitude sensor 58 are common to, and operate with, both fluid dispensing and vacuum evacuating sub-systems 62, 64 and 66, 68. Providing a second independently operable set of sub-systems 64, 68 allows the caregiver to treat two wounds using a single apparatus 2. Accordingly, second fluid dispensing and evacuating sub-systems 64, 68 also shown in FIG. 2, comprise identical components as discussed regarding sub-systems 62, 66 and are labeled in a corresponding manner. For example, syringe motor drive 72 in sub-system 62 is identified as syringe motor drive 172 in sub-system 64, and a vacuum pump 110 in sub-system 66 is identified as vacuum pump 210 in sub-system 68.

A schematic diagram of a portion of wound treatment apparatus 2 is shown in FIG. 3. Each system 6 and 8 is configured to operate in the same manner. Specifically, FIG. 3 depicts the operation of system 6. Movement of plunger 70 into syringe 24 causes fluid stored in syringe 24 to exit into tube 18 and into bandage 314 where it drains through orifices 302 onto wound 300. Vacuum 110 applies a negative pressure through waste canister 26 and bandage 314. Fluid and exudate are then drawn from wound 300 out through tube 20 and into canister 26. The hydrophobic filter 108, discussed in connection with FIG. 2, allows the vacuum to pass through waste canister 26, yet, prevents any of the fluid from escaping, and depositing the fluid into pump 110.

Figure 4:
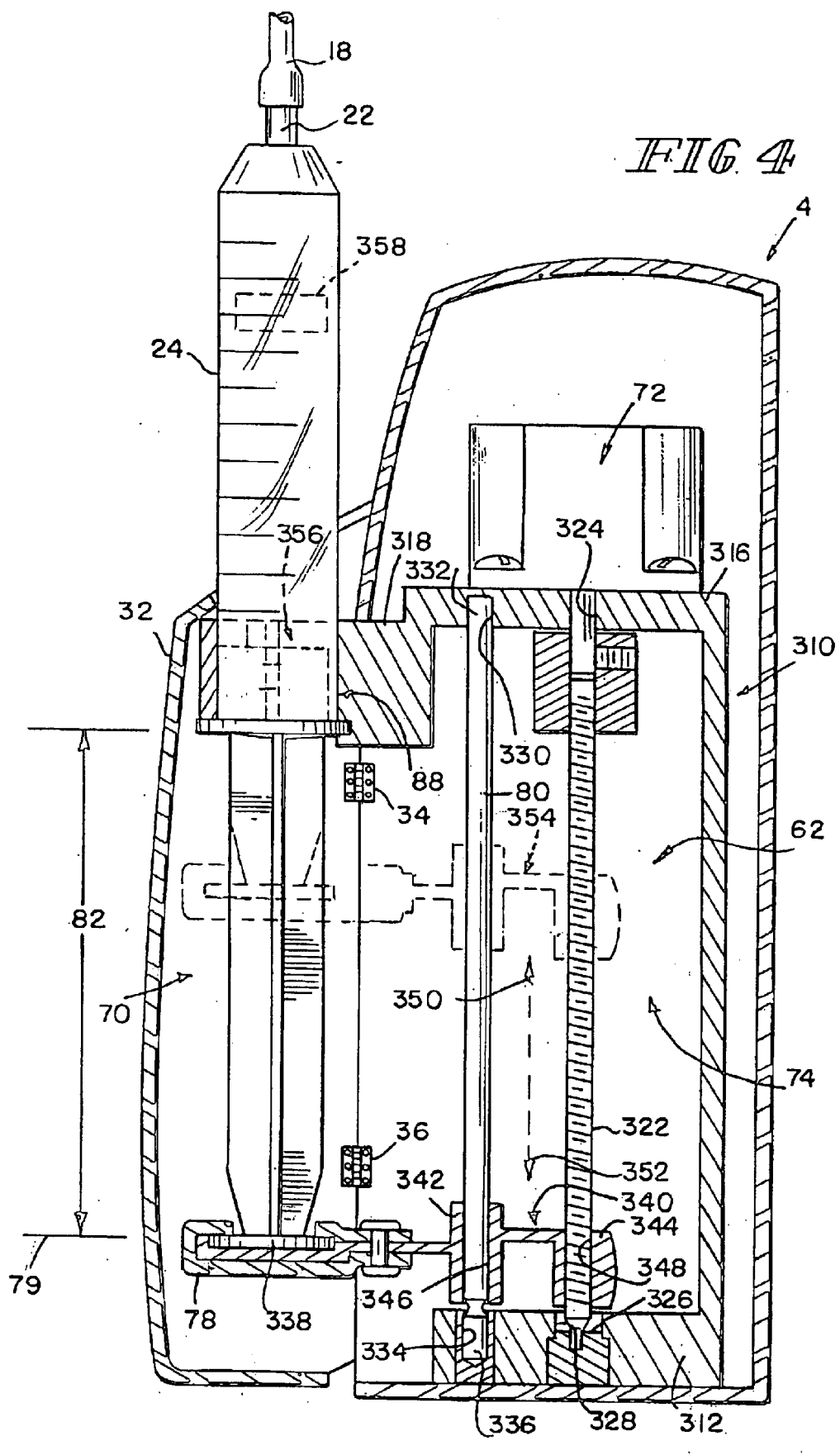
FIG. 4 is a side cross-sectional view of the wound treatment apparatus along the lines A—A of FIG. 1.

The mechanism for moving plunger 70 into syringe 24, part of fluid dispensing sub-system 62, is shown in cross-sectional form in FIG. 4. The illustrated embodiment includes sub-system 62 positioned within housing 4. Specifically, a bracket frame 310 serves as the skeletal structure for sub-system 62. Bracket 310 includes a base portion 312 with an upwardly extending structural member 314 appending from one end thereof. A support portion 316 extends outwardly from member 314, and is superposed above base portion 312. Extending from support portion 316 is syringe bracket 318. Syringe capture mechanism 88 is formed in bracket 318, and is configured to receive syringe 24, as previously discussed. Bracket 318 and capture mechanism 88 are configured to suspend syringe 24 with luer-lok port 22 directed upwardly. It is contemplated that capture mechanism 88 secures syringe 24 to bracket 318 by other means, including being friction-fitted, or secured with clips or bolts. To move plunger 70, syringe drive 74 and plunger interface 78 are coupled to frame 310. Plunger interface 78 captures plunger 70 and provides upward linear motion to evacuate syringe 24. Interface 78 provides a release mechanism for plunger 70 to remove syringe 24 at any position in the stroke.

Syringe drive 74 comprises syringe drive motor 72 and power screw 322. Power screw 322 is disposed through an aperture 324 in support portion 316, and is rotatably coupled to motor 72. It is appreciated that motor 72 can be a stepper or electric motor, for example. The lower end 326 of power screw 322 is positioned within a bearing cavity 328 within which power screw 322 rotates. Spaced in parallel to power screw 322 is guide 80. Guide 80 is received in an aperture 330, also disposed in support portion 316 at its upper end 332, and is received in cavity 334 at its lower end 336. Plunger interface 78 is configured to receive cap 338 of plunger 70, and is coupled to a dual coupler 340. Dual coupler 340 comprises two blocks 342, 344, each having bores 346, 348 disposed, respectively, there through. In the illustrated embodiment, bore 346 has a smooth surface and is configured to receive guide 80. In contrast, bore 348 has a threaded surface and is configured to cooperate with threads on power screw 322. Coupler 340 is movable upwardly and downwardly in directions 350, 352. A hatched outline version of coupling 340, indicated by reference numeral 354, is shown depicting plunger interface 78 and plunger 70 moving upwardly in direction 350. As shown in FIG. 4, as plunger 70 is moved upwardly, head 356 is also moved upwardly, reducing the available space in syringe 24, thus, displacing any fluid in syringe 24 out of luer-lock port 22, thereby dispensing the fluid into tube 18 and into bandage 14. The movement of cap 356 is depicted by the position of cap 356 in hatched lines moved to an upper position indicated by reference numeral 358.

Figure 6:
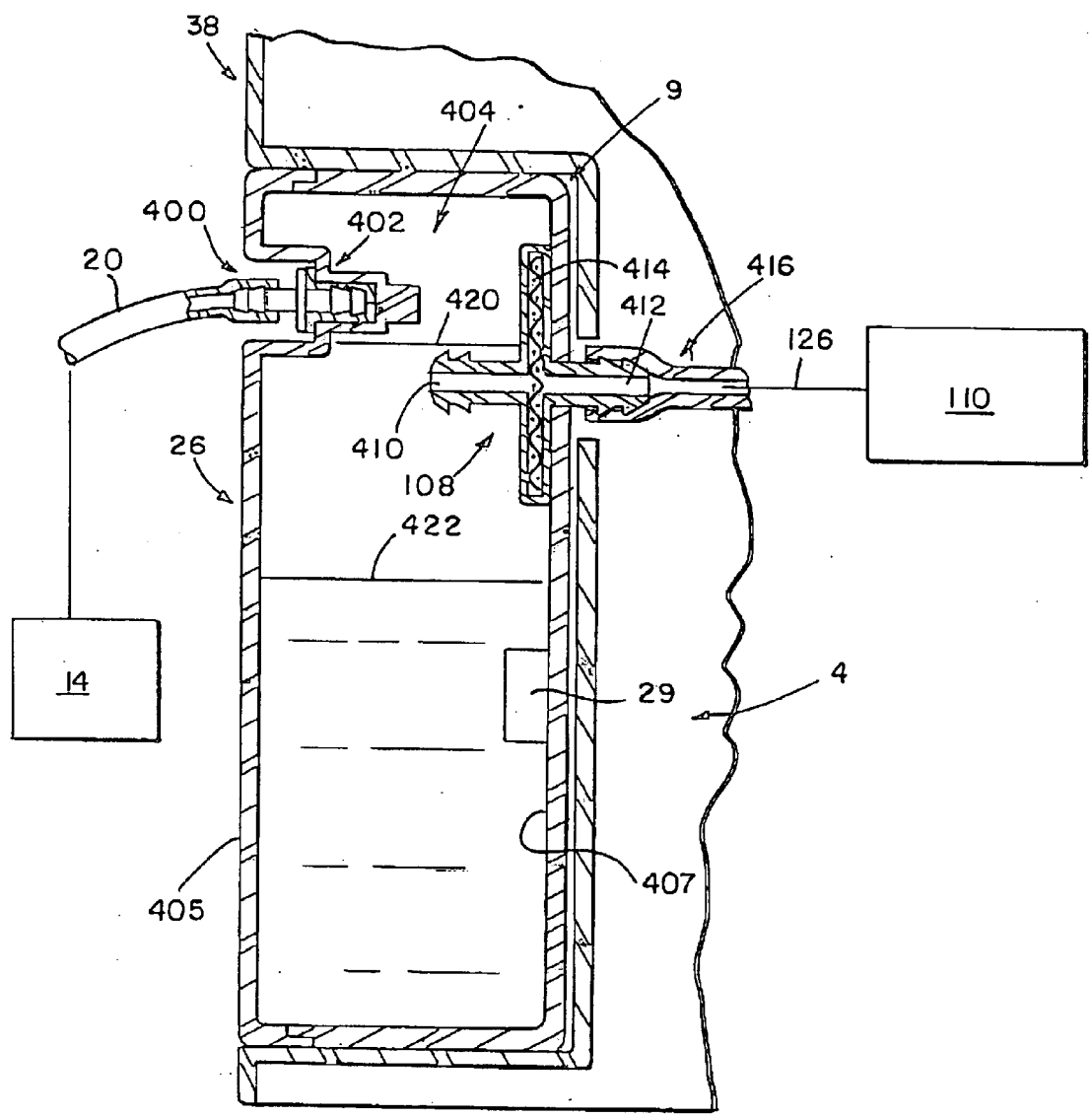
FIG. 6 is a cross-sectional view of a waste disposal canister of the wound treatment apparatus along the lines B—B of FIG. 1.

A cross-sectional view of waste canister 26 located in cavity 9 on side 38 of housing 4 is shown in FIG. 6. Tube 20 is connected to a check-valve assembly 400 coupled to recess 402 disposed in the front wall 405 of canister 26. Check valve 400 is configured to allow fluid and exudate from bandage 14 to enter canister 26 and deposit in holding space 404 within canister 26, yet prevent any fluid already in space 404 from exiting through valve 400. Check valve 400, thus prevents fluid from escaping when tube 20 is disengaged from valve 400. In addition, canister 26 can be discarded without any fluid escaping. Hydrophobic filter 108 is located on the rear wall 407 of canister 26. A liquid solidifier 29 is provided in space 404 to decease the fluidity of the exudate. This is a safety measure to lessen the chance of splashing or run-off if canister 26 (or 27) is opened or broken.

Filter 108 in canister 26 is shown having an inlet 410 provided in space 404 and an outlet 412 coupled to a connector 416 with a barrier of hydrophobic material 414 provided there between. As previously discussed, the hydrophobic material allows the vacuum to pass through inlet 410 and outlet 412, yet prevents any fluid from passing. Similar to check valve 400, hydrophobic filter 108 too prevents any fluid from escaping even when canister 26 is removed from housing 4. Outlet 412 of filter 108 is in communication with connector 416. Connector 416 is configured to receive and seal outlet 412 when canister is positioned in cavity 9. Connector 416 is in communication with line 126 and ultimately with pump 110.

In the illustrated embodiment, hydrophobic filter 108 serves as both the canister full mechanism 114 that shuts off the vacuum supply to the canister 26 when the fluid level exceeds the "full" level as indicated by reference numeral 420. When the fluid level is below inlet 410, as indicated by reference numeral 422, fluid continues to enter space 404 through valve 400. When the fluid level 420 is above inlet 410, the fluid is acting as an air block. Fluid cannot pass through filter 108, but because the fluid level is above inlet 410, air cannot pass through either. This causes a dramatic pressure drop (vacuum increase) through line 126. Vacuum pressure transducer 124 is coupled to line 126 measuring the negative pressure passing through canister 26, as previously discussed. If such a dramatic pressure drop occurs, transducer 124 will provide such data to controller 50 through line 128. Controller 50 will then know to shut the system down until the full canister is replaced with either an empty or only a partially full canister.

Figure 8:
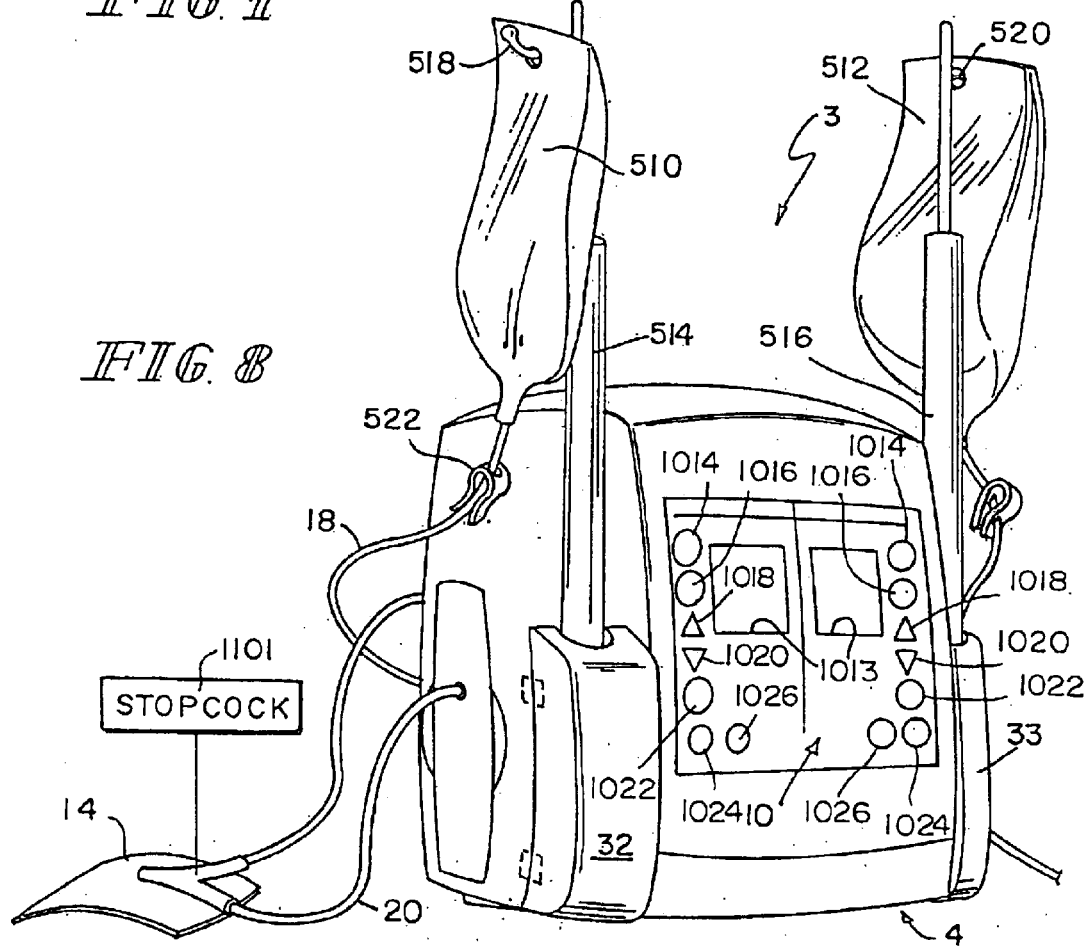
FIG. 8 is a perspective view of another embodiment of the wound treatment apparatus.

Another illustrative embodiment of a wound treatment apparatus is shown in FIG. 8 and is indicated by reference numeral 3. Apparatus 3 operates in a similar manner as apparatus 2, with the exception of the use of two "intravenous-style" fluid bags 510, 512 suspended above housing 4 to dispense the fluid. In this illustrated embodiment, posts 514, 516 with hooks 518, 520 extend upwardly of apparatus 3 from behind doors 32, 33. It will be appreciated that the posts 514, 516 may be extensible to elevate the bags 510, 512 to selected heights to provide selected pressures for irrigation. A dispensing tube 18 extends from each bag 510, 512 at one end and couples to each bandage. Gravity assists in moving fluid through tubes 18 and into the bandages. A tube clip 522 is coupled to each tube 18 and configured to pinch and close tube allowing the caregiver to selectively prevent fluid from dispensing into bandages.

Illustrative vacuum bandage 314 of FIG. 3 is designed to provide a protective environment around wound 300. Illustratively, such bandages last for up to 7 days without having to be replaced. Bandage 314 includes rinse and drain orifices (not shown) within the body of bandage 314 that communicate with tubes 18, 20, respectively. Such orifices are illustratively 0.030-inch (0.08 cm) diameter and/or 0.040-inch (0.10 cm) diameter. Vacuum evacuating sub-system 66 cooperates with bandage 314, similar to bandage 14, to draw the fluid and exudate from the surface of wound 300, and collect same into waste canister 26.

Examples of bandages 14 and 15 are shown in U.S. patent application Ser. No. 09/725,352, entitled VACUUM THERAPY AND CLEANSING DRESSING FOR WOUNDS, filed on Nov. 29, 2000, and assigned to the same Assignee or Affiliated Assignee as the present disclosure, and the complete disclosure of which is hereby expressly incorporated by reference. It is further contemplated that other bandages may be used with this control system, including bandages having separate irrigation and vacuum ports. Examples of such bandages are shown in U.S. patent application Ser. No. 09/369,113, entitled WOUND TREATMENT APPARATUS, filed on Aug. 5, 1999, and assigned to the same Assignee or Affiliated Assignee as the present disclosure, and the complete disclosure of which is hereby expressly incorporated by reference. The complete disclosure of U.S. patent application Ser. No. 10/144,504, entitled VACUUM THERAPY AND CLEANSING DRESSING FOR WOUNDS and filed on May 13, 2002, is hereby expressly incorporated by reference.

Figure 9:
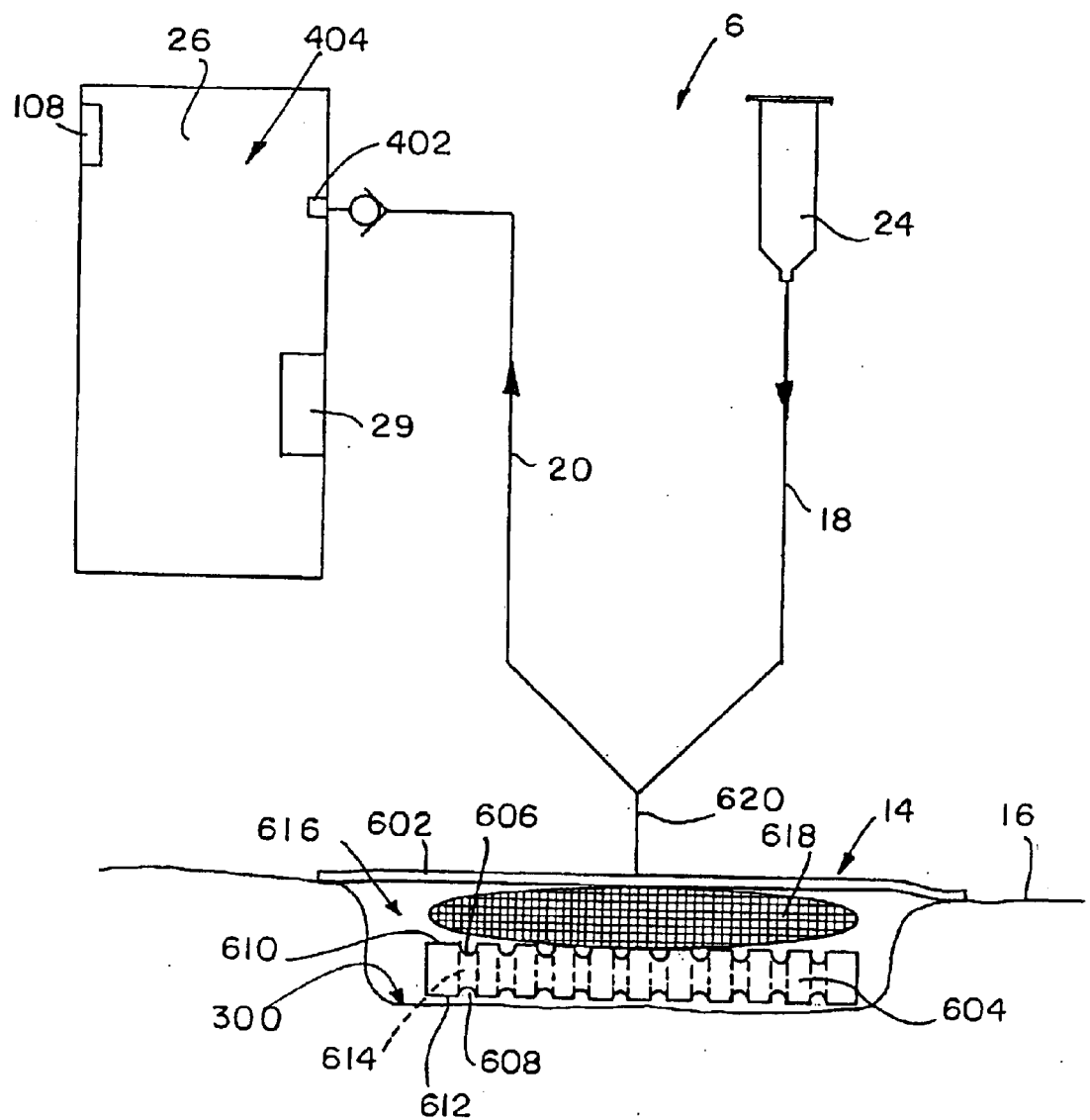
FIG. 9 is a side diagrammatic view of the vacuum bandage and portions of the wound treatment apparatus of FIG. 1.

A side diagrammatic view of bandage 14 along with a portion of system 6 is shown in FIG. 9. (See also FIG. 1.) Bandage 14 is of an illustrative type for use with apparatus 2. (Note that the bandage is not drawn to scale.) As previously discussed, bandage 14 is a vacuum bandage. Bandage 14 comprises a cover film 602, illustratively a flexible cover, that seals wound 300 about its outer perimeter. It is contemplated, however, that film 602 can be made from an occlusive or semi-occlusive material that allows water vapor to permeate there through, but otherwise protects wound 300 from the outside environment. A bandage member 604 is placed adjacent wound 300 and is configured to irrigate wound 300. In the illustrated embodiment, bandage member 604 comprises upper channels 606 and lower channels 608, each provided on opposite sides 610, 612, respectively, of bandage member 604. Each of the upper channels 606 is generally congruent with one of the lower channels 608. Channels 606 and 608 are in communication with each other via apertures 614. As shown in the illustrated embodiment, side 612 of bandage member 604 faces wound 300, and side 610 faces a porous packing 618. Packing 618 provided under film 602 to assist in providing a space 616 to facilitate the negative pressure. Packing 618 is typically a gauze material. It will be appreciated, however, that, for some wound care applications, the packing 618 will not be used with member 604 under the film 602.

Illustratively, the caregiver may activate system 6, by means previously described, to draw exudate from wound 300 through channels 606, 608 and apertures 614 of bandage member 604, packing 618 and film 602, through splitter tube 620 connected to evacuating tube 20, and deposit in canister 26. The negative pressure applied to wound 300 created by pump 110 can be applied for a period of time as determined by the caregiver. After a period of drawing, the caregiver may deactivate the negative pressure. The caregiver may begin irrigating wound 300 by releasing fluid from syringe 24, through tube 18, into splitter tube 620, through film 602 and packing 618, and into bandage member 604. The fluid will travel through channels 606 deposit in apertures 614 and irrigate wound 300 by traveling through channels 608. Illustratively, the fluid will continue to irrigate wound 300 until space 616 can no longer receive any more fluid. The fluid is held in space 616 for a period of time as determined by the caregiver. After that period, pump 110 is reactivated and the fluid and exudate from wound 300 is evacuated from bandage 14 and into canister 26 by the manner previously described. This process is repeated as many times as necessary as determined by the caregiver.

In one embodiment, user interface 10 comprises a momentary switch (not shown) that selectively operates the aforementioned process. For example, the switch may be configured such that when the caregiver depresses and holds the switch, the fluid will dispense from syringe 24 into bandage 14. When the caregiver releases the switch the fluid will stop dispensing and pump 110 will activate and begin drawing the fluid and exudate. It is contemplated that the switch may be configured to delay between the vacuuming and dispensing for a period of time that is definable by the caregiver. It is also contemplated that all of the aforementioned descriptions as applied to system 6 are applicable to system 8.

The apparatus 2 is a portable, easy to use topical system that is intended to provide a protective/occlusive environment with features to facilitate the administering of standard wound care. The apparatus 2 provides for the care of two independently controlled wounds. The apparatus 2 provides negative pressure to the wound bed, and the caregiver can set the level of negative pressure. Illustratively, the negative pressure is variable from 25-mmHg to 175-mmHg at increments of 10 mmHg. The caregiver can choose between continuous, intermittent (profile), and no negative pressure modes. It will be appreciated that the apparatus 2 may be set up to provide various levels of vacuum at various times. The apparatus may be provided with the ability to pause negative pressure therapy for set durations of time. The system may be set up to provide audible alarms to remind the caregiver to reset or start a new cycle of vacuum therapy.

The apparatus 2 is intended to provide an occlusive wound healing environment. The apparatus 2 provides an active therapy unit that delivers drainage and cleansing for aggressive wound healing. It is intended, for example, for use on all pressure ulcers (Stage II through Stage IV), surgical draining wounds and leg ulcers.

Figure 7:
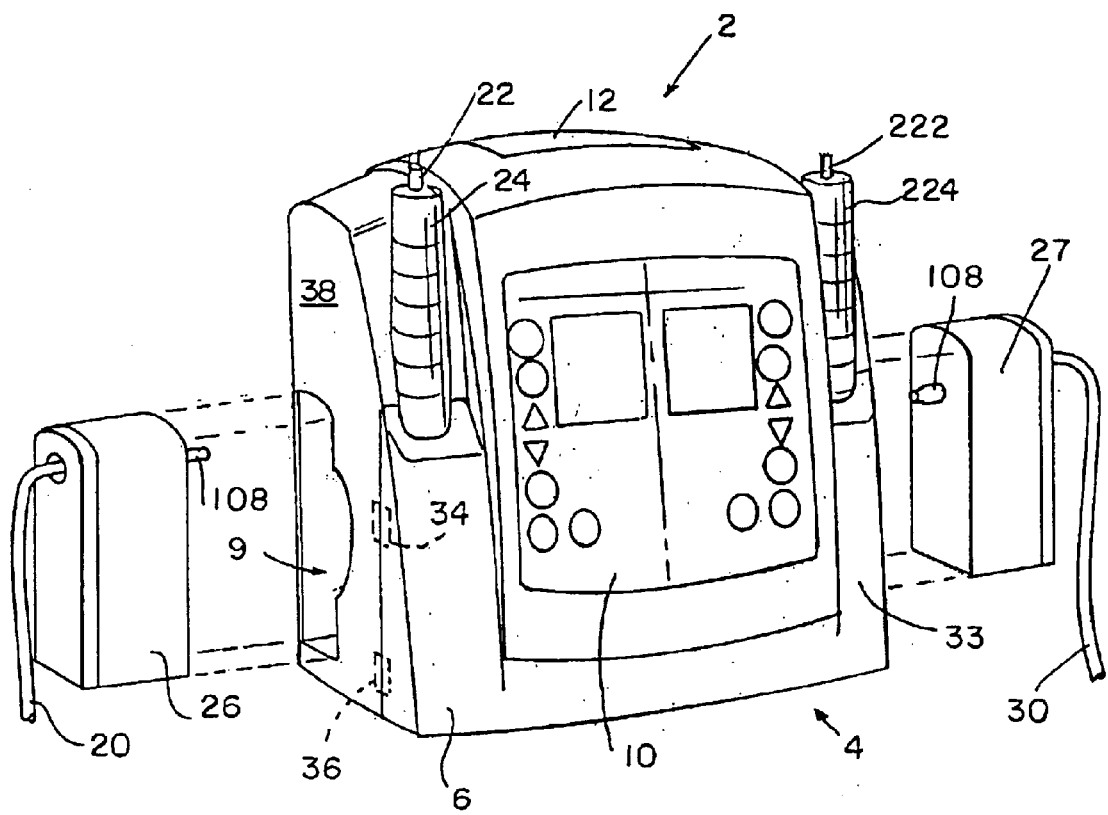
FIG. 7 is a partially exploded perspective view of the wound treatment apparatus of FIG. 1 with the waste canisters removed.
Figure 10:
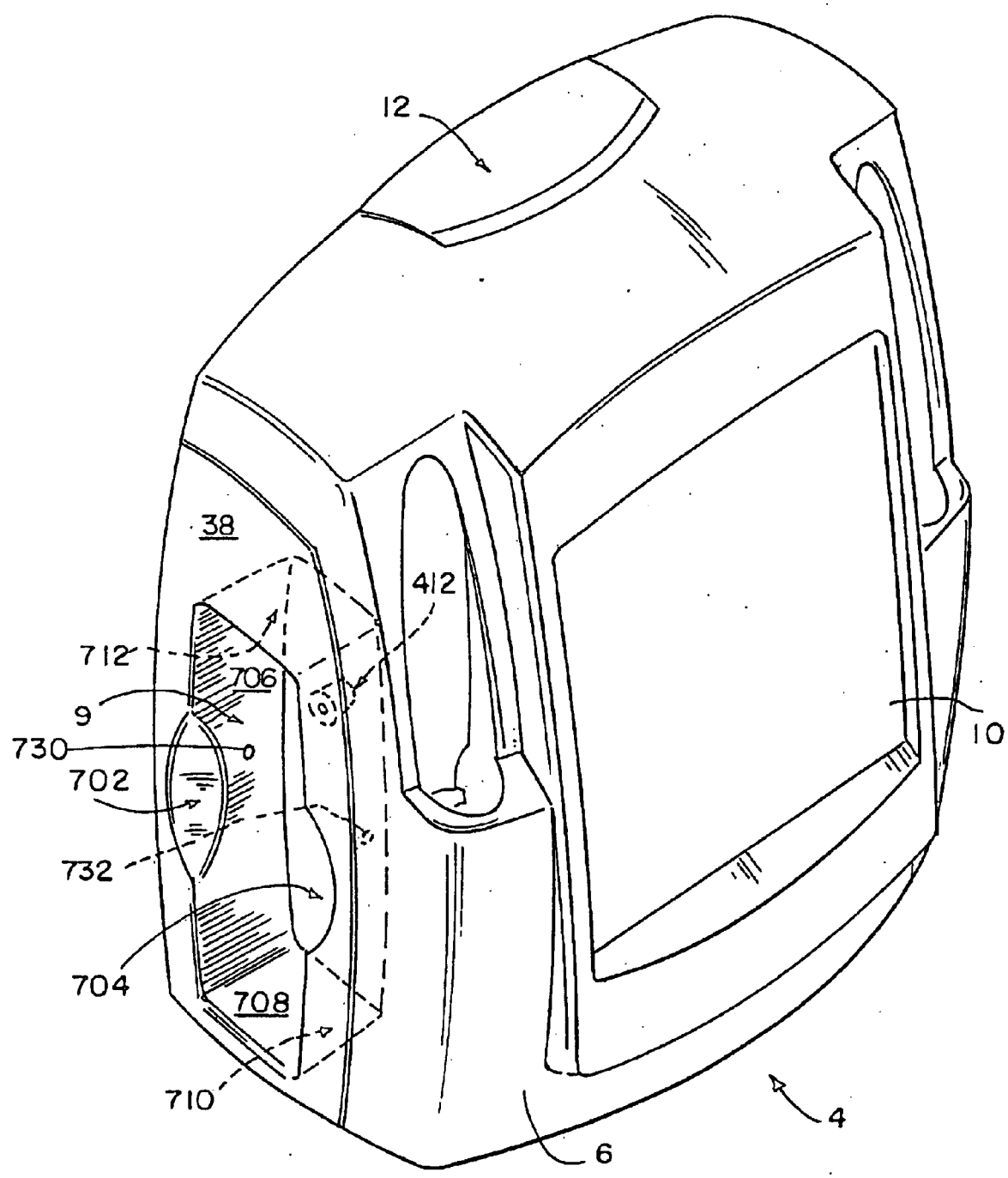
FIG. 10 is a perspective view of the wound treatment apparatus of FIG. 1 with the waste canister removed.
Figure 11:
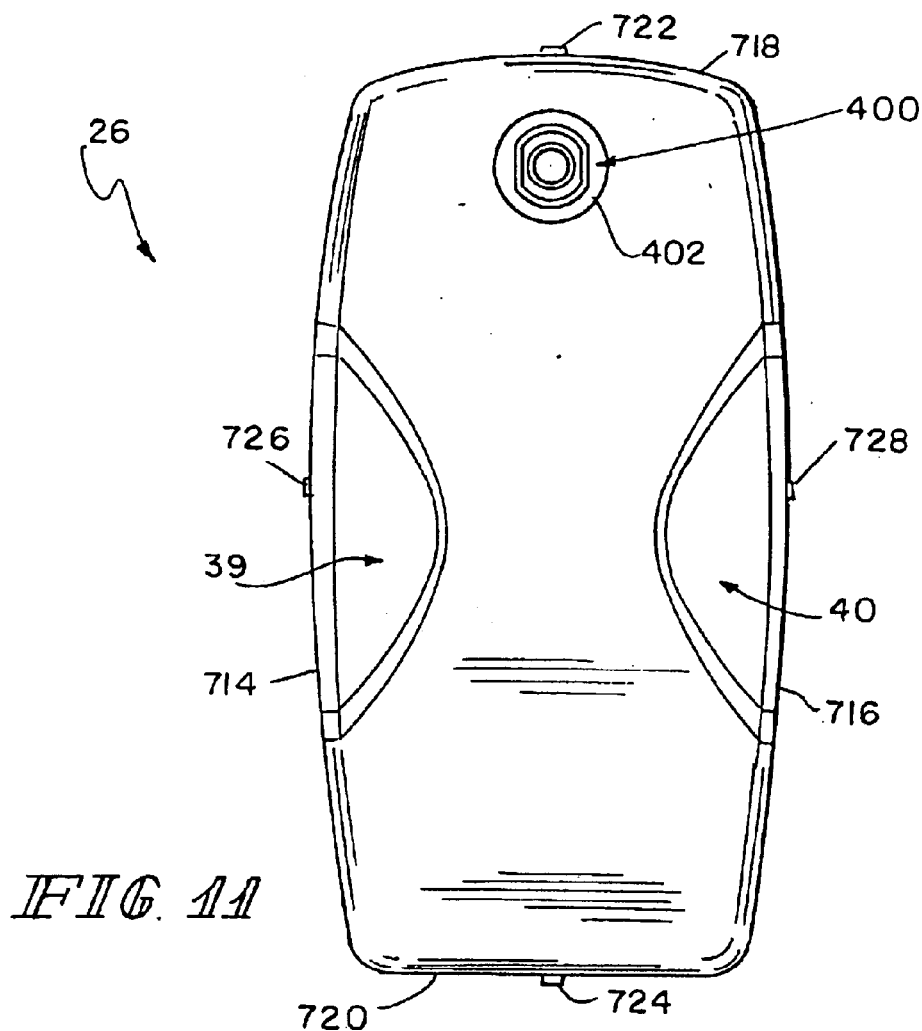
FIG. 11 is a front elevational view of a waste canister.
Figure 13:
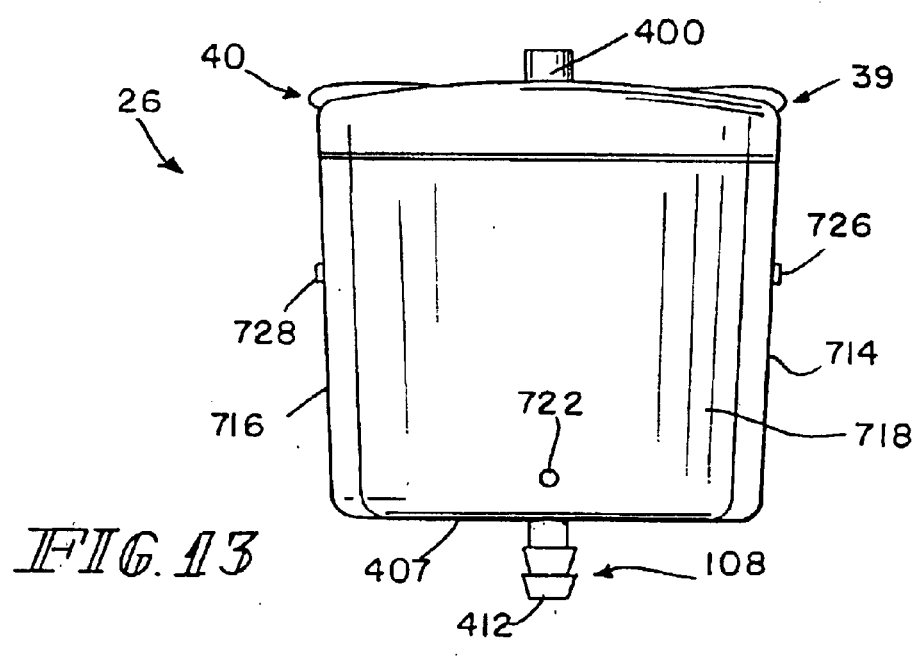
FIG. 13 is a top view of the waste canister of FIG. 11.
Figure 12:
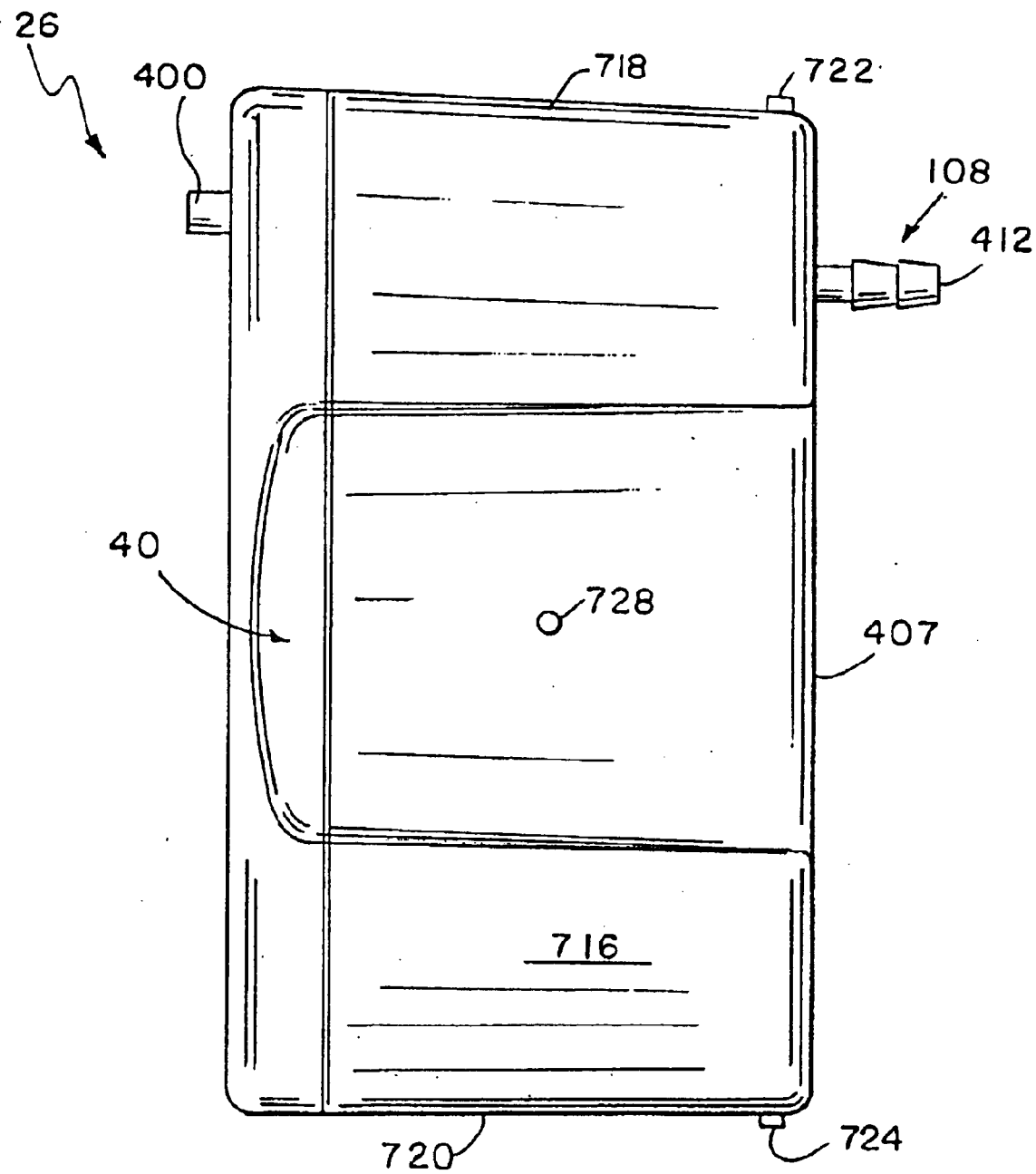
FIG. 12 is a side elevational view of the waste canister of FIG. 11.

In the illustrated embodiment, as shown in FIGS. 7 and 10, for example, canister 26 is configured to be received in cavity 9 disposed in side 38 of housing 4. As shown specifically in FIG. 10, cavity 9 comprises two pull recesses 702, 704. Such recesses 702, 704 are concave-shaped portions formed adjacent to side 38 and to side walls 706 and 708. Recesses 702, 704 are provided to allow finger clearance when the caregiver grasps grip portions 39, 40 of canister 26 to remove it from, or insert it into cavity 9. (See also FIGS. 1, 11 and 13.) Side walls 706, 710 and bottom and top walls 708, 712 define cavity 9 such that cavity 9 provides a relatively conforming receptacle for the canister 26. The walls 706, 710 and 708, 712 conform to the size and shape of the panels 714, 716, 718, 720 of canister 26. (See FIGS. 12 and 13.) Outlet 412 of filter 108 mates with connector 416 to produce an air-tight seal between port 412 and connector 416. It is further contemplated that other structures or configurations of outlet 412 and connector 416 can be used to ensure system 6 is a closed system when canister 26 is properly coupled to housing 4. It is still further contemplated that the aforementioned descriptions of canister 26 of system 6 apply equally to canister 27 of system 8.

Each of top and bottom panel 718, 720 of canister 26 includes a boss 722, 724, respectively. Each boss 722, 724 is configured to engage a sensor such as sensor 116, 118, respectively, as depicted in FIG. 2. This engagement provides a signal to controller 50 indicating that canister 26 is seated properly into cavity 9 and the vacuum therapy treatment may begin to be administered. It is contemplated that bosses 722, 724 can be mechanical sensors, optical, capacitive or other similar type sensors.

Side panels 714, 716 include buttons 726, 728 to assist the caregiver in placing canister 26 in the proper location within cavity 9. Illustratively, buttons 726, 728 are small protrusions, each extending from a side panel. Each button 726, 728 is configured to be received or "snapped" into corresponding dimples 730, 732, respectively, disposed in walls 706, 710, respectively. In the illustrated embodiment, the buttons extend from the widest point of side panels 714, 716 of canister 26.

Figure 14:
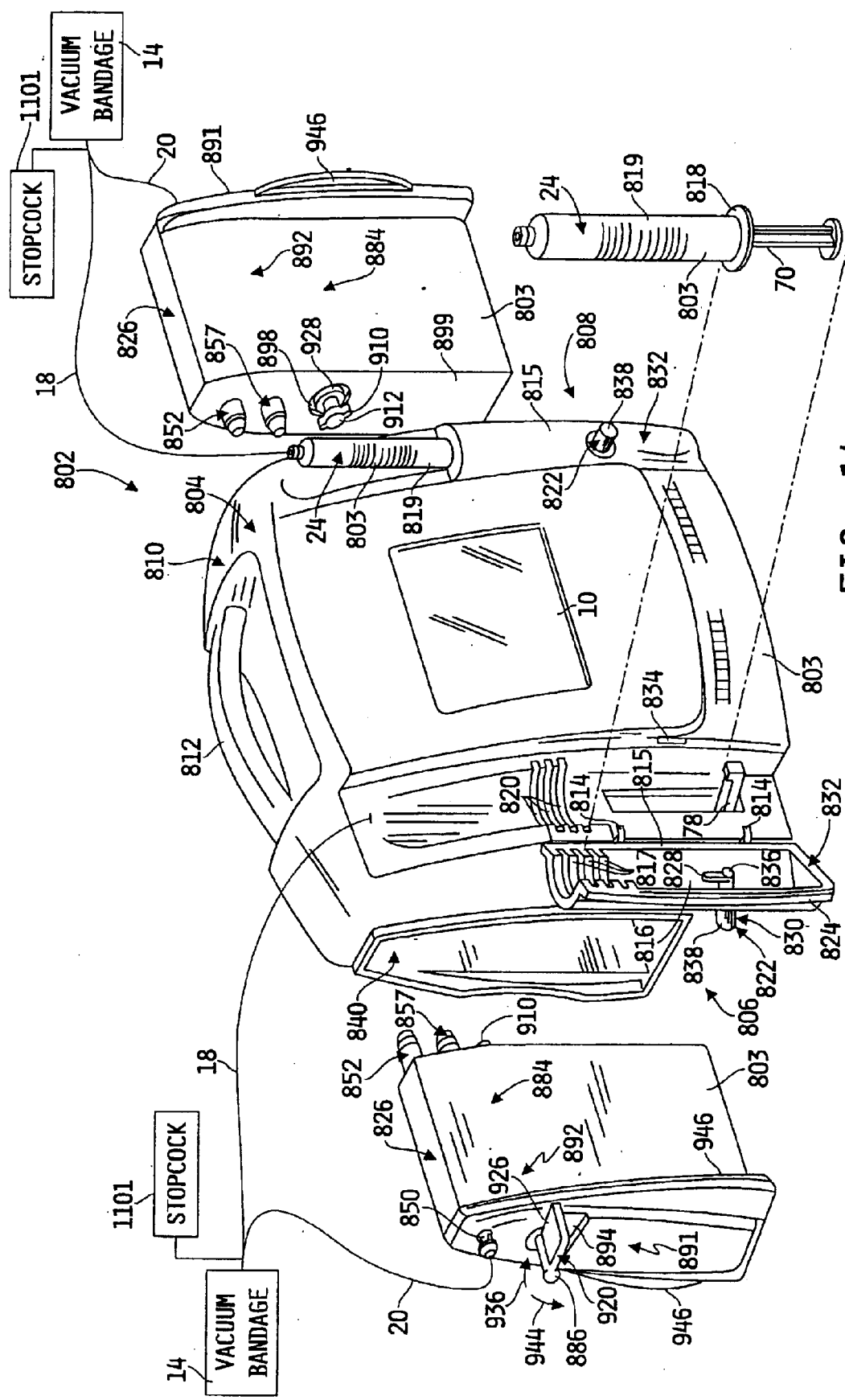
FIG. 14 is a perspective view of another wound treatment apparatus showing a pair of canisters arranged for insertion into respective receptacles formed in the sides of a housing of a control unit and showing a fluid source arranged for insertion into a receptacle formed in the front of the housing.

Another wound treatment apparatus 802 is illustrated in FIG. 14. Apparatus 802 is similar in structure and function to apparatus 2, except as otherwise noted, so that identical reference numbers refer to similar components. Apparatus 802 has a pair of vacuum wound bandages 14, a pair of dispensing lines 18, a pair of evacuating lines 20, and a main control unit 803 adapted for use with bandages 14 and lines 18, 20. Bandages 14, lines 18, 20, and control unit 803 cooperate to provide dual vacuum therapy systems 806, 808.

Control unit 803 has a control module 810, a pair of fluid sources such as syringes 24 coupled to dispensing lines 18 to provide fluid for irrigation of the wounds, and a pair of disposable waste collection canisters 826 coupled to evacuating lines 20 to collect waste material such as exudate from the wounds and fluid from syringes 24, as illustrated in FIG. 14. Each dispensing line 18 and evacuating line 20 is associated with one of bandages 14. Each syringe 24 and canister 826 is provided for one of systems 806, 808. Control module 810 has a housing 804. Syringes 24 are coupled to the front of housing 804 and canisters 826 are coupled to the sides of housing 804, as discussed in more detail below. Housing 804 has a handle 812 at the top thereof for hand-carrying control unit 803. A user interface 10 is centrally mounted to housing 804 between syringes 24 and canisters 826 to allow a caregiver to operate systems 806, 808.

Systems 806, 808 are similar to one another in structure and function. Thus, the following description of system 806 applies also to system 808.

Figure 17:
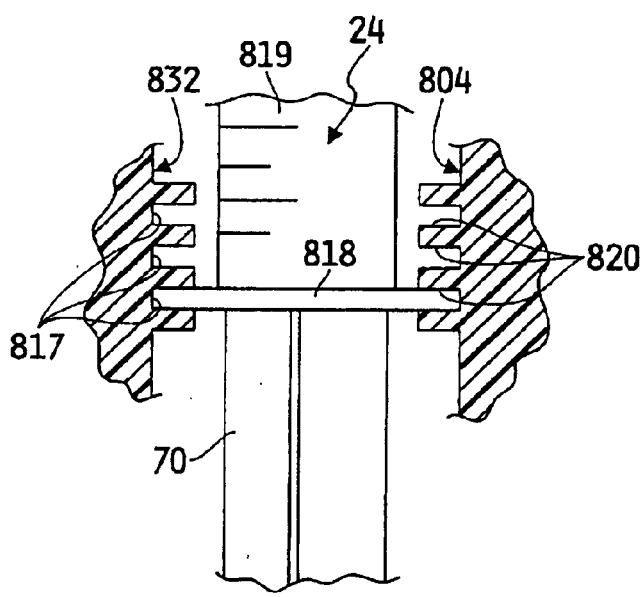
FIG. 17 is a fragmentary sectional view showing a syringe having a flange received by grooves of the door and the housing to retain a barrel of the syringe in place.

Housing 804 has a door 832 to partially cover syringe 24, as illustrated in FIG. 14. Door 832 is hinged to housing 804 by a pair of vertically-spaced hinges 814 positioned along a laterally outer side 815 of door 832 for movement of door 832 between opened and closed positions. A rear side 816 of door 832 has a plurality of vertically-spaced, horizontal mounts or grooves 817 (see FIGS. 14 and 17) for receiving a flange 818 of syringe 24. Housing 804 also has a plurality of corresponding vertically-spaced, horizontal mounts or grooves 820 (see FIGS. 14 and 17) for receiving flange 818. During installation of syringe 24, an end of a plunger 70 of syringe 24 is placed on a vertically movable plunger interface 78 of a syringe drive mechanism, such as the one described above in connection with apparatus 2, and flange 818 is inserted into one of grooves 820. Door 832 is then closed causing one of grooves 817 to receive flange 818 so that syringe 24 is held in place by grooves 817, 820. Grooves 817, 820 support syringe 24 in a vertical orientation.

Figure 15:
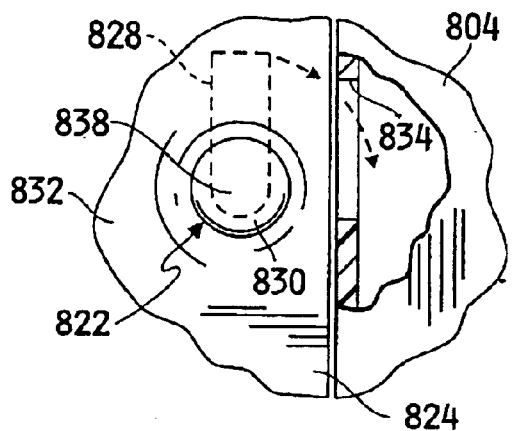
FIG. 15 is an enlarged elevation view of a latch for a door of the wound treatment apparatus of FIG. 14 showing the latch in a release position.
Figure 16:
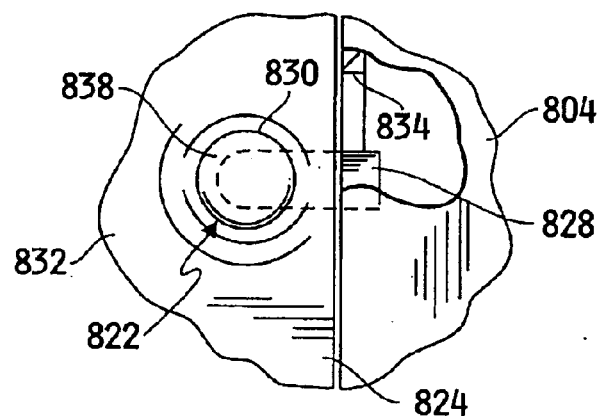
FIG. 16 is a view similar to FIG. 15 showing the latch in a latched position.

A door latch 822 is coupled to a laterally inner side 824 of door 832, as illustrated in FIGS. 14–16. Latch 822 is movable relative to door 832 between a latched position (FIG. 16) blocking movement of door 832 from its closed position to its opened position and a release position (FIGS. 14–15) allowing door 832 to move between its closed position and its opened position. Latch 822 has a fastener 828, such as an arm or lug, and an actuator 830 to pivot fastener 828 into and out of a slot 834 of housing 804 between the latched and release positions. Actuator 830 has a stem 836 coupled to fastener 828 and a handle or door knob 838 coupled to stem 836 to rotate stem 836 and thus fastener 828 between the latched and release positions when a caregiver rotates handle 838. Stem 836 extends through an aperture of door 832. Handle 838 is coupled to one end of stem 836 in front of door 832 and fastener 828 is coupled to an opposite end of stem 836 behind door 832.

Figure 27:
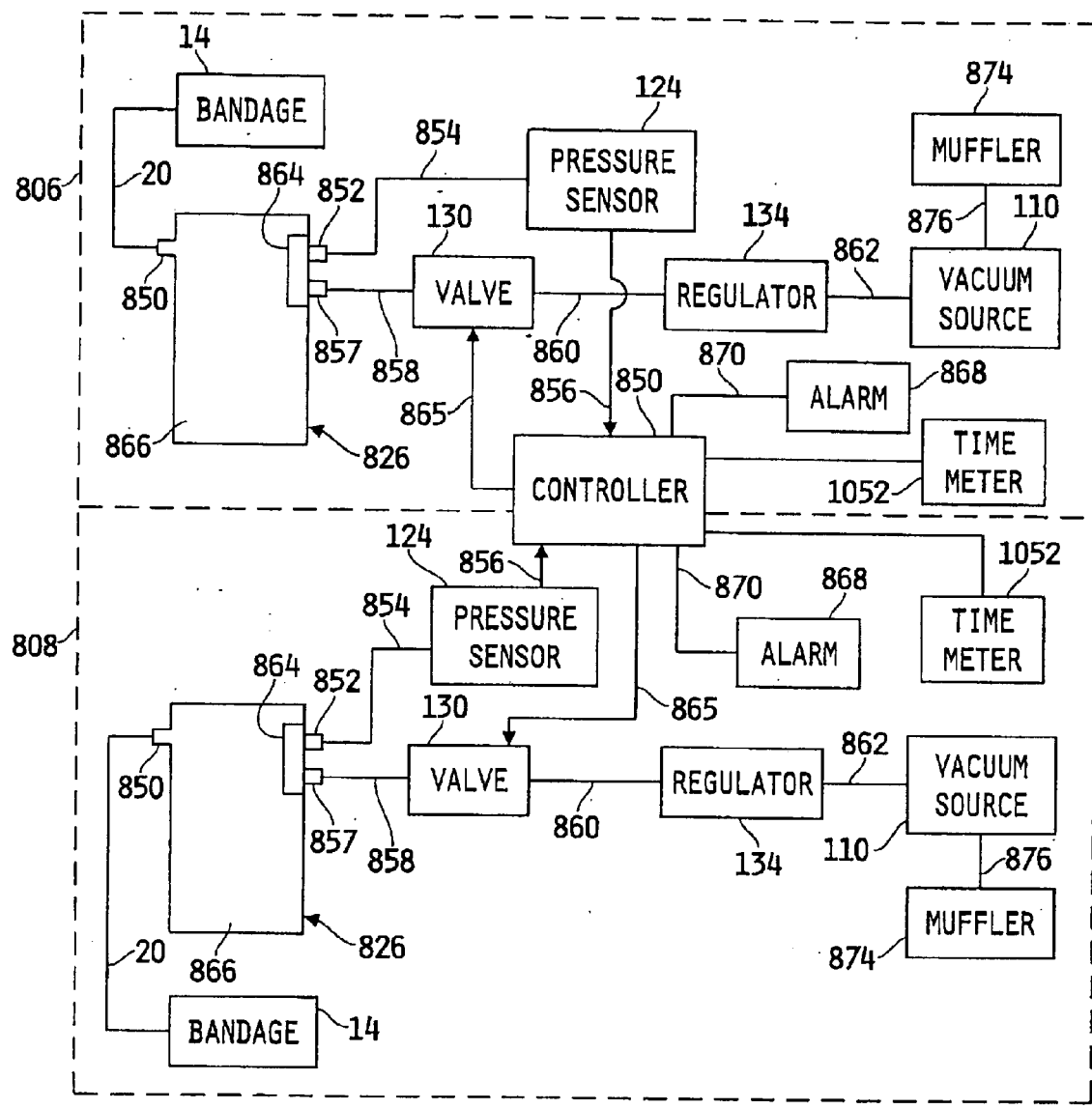
FIG. 27 is a diagrammatic view of portions of the wound treatment apparatus of FIG. 14.

Canister 826 is coupled to vacuum bandage 14 and other components of apparatus 802, as illustrated, for example, in FIG. 27. Evacuating line 20 is coupled to vacuum bandage 14 and an inlet port 850 of canister 826 to introduce waste material into an interior region or chamber 866 of canister 826 through inlet port 850. A pressure sensor 124 is coupled to an upper pressure port 852 of canister 826 via a fluid line 854 (see FIGS. 19 and 27) to sense the pressure in region 866. Pressure sensor 124 sends a signal indicative of the sensed pressure to a controller 850, which is common to both systems 806, 808, via an electrical line 856 (see FIG. 27). A proportional valve 130 (see FIGS. 19 and 27) is coupled to a lower outlet port 857 of canister 826 via a fluid line 858 (see FIGS. 19 and 27). A pressure regulator 134 (see FIGS. 19 and 27) is coupled to proportional valve 130 and a vacuum source 110 (see FIGS. 19 and 27) via fluid lines 860 and 862, respectively (see FIG. 27). Vacuum source 110 provides a negative or vacuum pressure within bandage 14 through lines 862, 860, 858, 20 and regulator 134, valve 130, and canister 826 to suction waste material into canister 826.

Vacuum source 110 continues to operate even if, for example, blockage occurs somewhere upstream from vacuum source 110. If the blockage becomes too great, vacuum source 110 could experience too great a load, or vacuum pressure. Pressure regulator 134 is provided to establish a maximum load that vacuum source 110 can experience. Pressure regulator 134 allows air to be suctioned into line 862 when this maximum load is reached to protect vacuum source 110.

Figure 20:
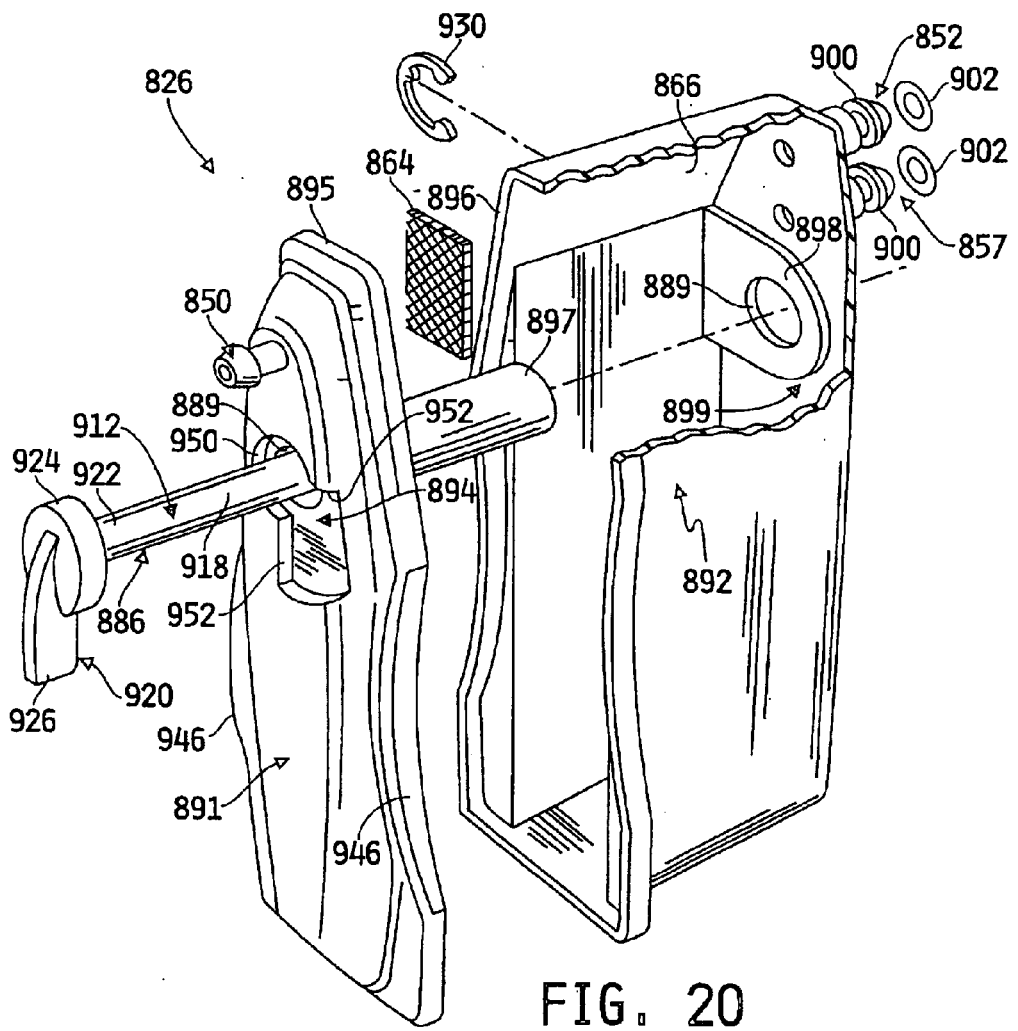
FIG. 20 is an exploded perspective view of a waste collection canister of the control unit.
Figure 23:
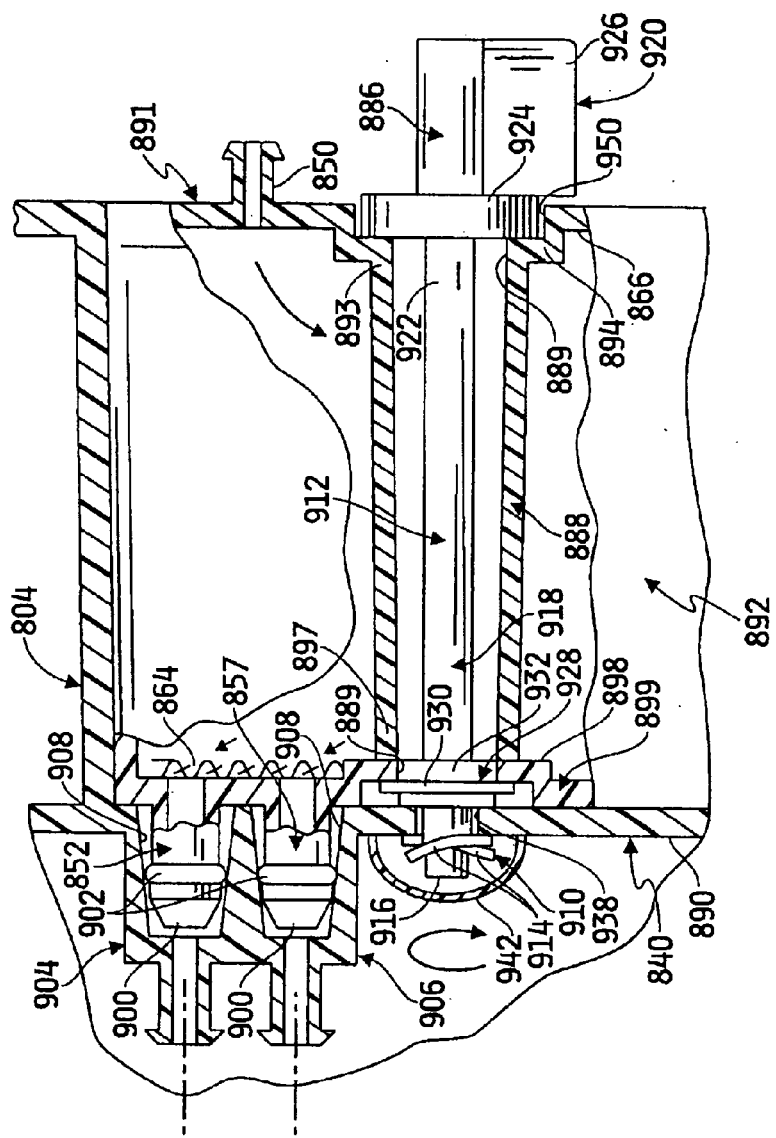
FIG. 23 is a side sectional view similar to FIG. 22 of the canister installed within the receptacle.

A filter 864 is positioned in interior region 866, as shown in FIGS. 20, 23, and 27. Filter 864 covers pressure port 852 and outlet port 857 to prevent waste material from entering lines 856, 858 and possibly damaging pressure sensor 124, proportional valve 130, pressure regulator 134, or vacuum source 110. Filter 864 is, for example, a 1.0 micron teflon hydrophobic filter.

Controller 850, pressure sensor 124, and proportional valve 130 cooperate to provide feedback control of the vacuum pressure provided to bandage 14. Controller 850 operates proportional valve 130 via electrical line 864 in response to the pressure sensed by pressure sensor 124 to provide a desired negative pressure in interior region 866. A caregiver provides the desired negative pressure to controller 850 through user interface 10. If, for example, pressure sensor 124 senses a pressure in canister 826 that is more negative than the desired negative pressure (which includes a suitable tolerance range), controller 850 will cause valve 130 to move closer toward its fully closed position so that interior region 866 experiences less of the suction from vacuum source 110 and the pressure in canister 826 rises to approach the desired negative pressure. On the other hand, if pressure sensor 124 sense a pressure in canister 826 that is more positive than the desired negative pressure, controller 850 will cause valve 130 to move closer to its fully opened position so that interior region 866 experiences more of the suction from vacuum source 110 and the pressure in canister 826 lowers to approach the desired negative pressure.

Based on readings from pressure sensor 124, controller 850 is able to detect when the waste material in canister 826 has reached a fill limit, which occurs when the waste material at least partially occludes outlet port 857. As outlet port 857 becomes occluded due to the wetting of filter 864, the negative pressure established by vacuum source 110 becomes blocked from interior region 866. The pressure sensed by sensor 124 then begins to rise (i.e., become less negative) above the desired negative pressure, especially if bandage 14 has a vent in communication with atmosphere, and air enters interior region 866 through bandage 14, line 20, and inlet port 850. In some embodiments, air enters interior region 866 through a bleed port (not shown) formed in housing 884 at an elevation higher than outlet port 857 instead of through the bandage vent or in addition to the bandage vent. In response to the pressure rise, controller 850 moves proportional valve 130 toward its fully opened position to try to lower the sensed pressure to the desired negative pressure. If vacuum source 110 is able to lower the sensed pressure to the desired negative pressure, the waste material fill limit has not been reached. If the sensed pressure remains above the desired negative pressure, controller 850 opens proportional valve 130 further and compares the sensed pressure to the desired negative pressure.

Controller 850 determines that the waste material in canister 826 has reached its fill limit when proportional valve 130 has been fully opened but the sensed pressure remains above the desired negative pressure. This occurs because the waste material has occluded outlet port 857 enough to prevent vacuum source 110 from being able to lower the sensed pressure to the desired negative pressure. Pressure sensor 124, however, is still able to sense the pressure within interior region 866 through pressure port 852 because pressure port 852 is positioned at an elevation higher than outlet port 857. Controller 850 then activates an alarm 868 via an electrical line 870 to alert a caregiver that canister 826 is full and needs to be changed.

Figure 18:
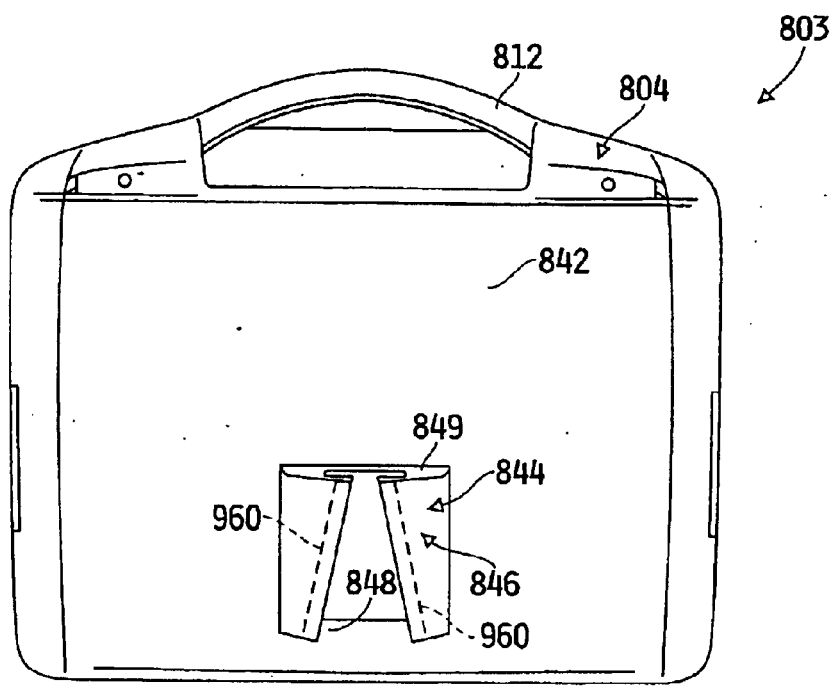
FIG. 18 is a perspective view of the rear of a control unit of the wound treatment apparatus of FIG. 14 showing a carrying handle at the top of the control unit and a mounting bracket on a rear wall of the control unit.
Figure 19:
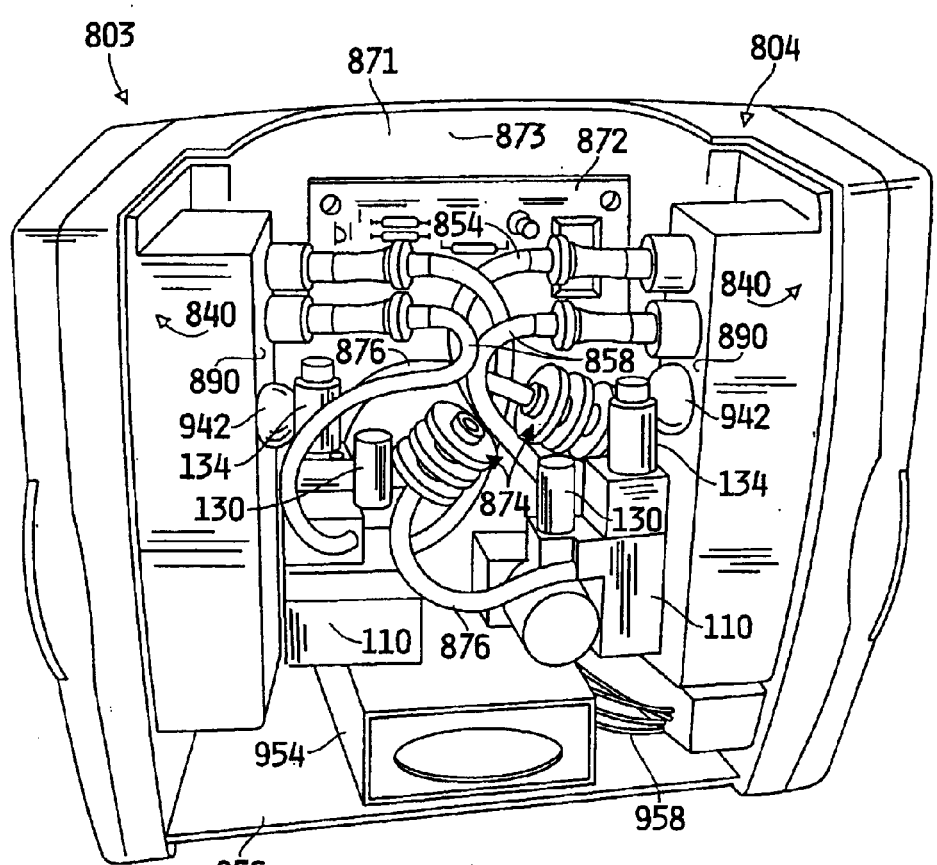
FIG. 19 is a perspective view of the rear of the control unit of FIG. 18 with a rear wall removed.

Housing 804 contains components of control unit 803, as illustrated in FIG. 19. Housing 804 has two receptacles 840, one receptacle 840 on each side of housing 804, and each receptacle 840 is configured to receive a respective canister 826 therein. Housing 804 also has a removable vertical rear wall 842 (see FIG. 18). Behind rear wall 842 is a chamber 871 (see FIG. 19). Each receptacle 840 extends toward a center of chamber 871 from a side wall of housing 804. A printed circuit board (PCB) 872 is mounted to a rear surface of a front wall 873 of housing 804 within chamber 871. Pressure sensors 124 and controller 850 are mounted to PCB 872 within chamber 871. Valves 130, pressure regulators 134, vacuum sources 110, and lines 854, 858 are also positioned within chamber 871.

A pair of mufflers 874 and a pair of muffler lines 876 are positioned within chamber 871. Each muffler line 876 is coupled to one of mufflers 874 and one of vacuum sources 110. Illustratively, each muffler 874 has three disk filters 878 in series to provide three chambers 880 having glass fiber material 882 therein to absorb sound energy. Adjacent filters 878 are coupled together by luer-lock mechanisms.

A battery 954 rests on a bottom wall 956 of housing 804 in chamber 871, as illustrated in FIG. 19. A main power connection 958 is coupled to battery 954 and to PCB 872. Battery 954 is illustratively a rechargeable nickel metal hydride battery that automatically recharges when main power connection 958 is coupled to an external electrical outlet (not shown) via a power cord (not shown), for example, and automatically provides electrical power to the electrical components of control unit 803 when battery 954 is charged and the power cord is disconnected from the external electrical outlet.

A mounting bracket 844 is coupled to an outwardly facing surface of rear wall 842, as illustrated in FIG. 18, to mount control unit 803 to a suitable control unit support (not shown). Bracket 844 has an envelope 846 to receive the support through a lower opening 848. A horizontal upper wall 849 is coupled to the top of envelope 846. Envelope 846 has internal tapered walls 960 extending from the bottom of envelope 846 to upper wall 849. The control unit support wedges against tapered walls 960 when it is inserted within envelope 846.

Canister 826 has a housing 884 providing interior region 866 to collect waste material therein and a latch 886 to couple housing 884 to housing 804 of control module 810, as illustrated in FIGS. 14 and 20–23. Canister 826 further has a cylindrical sleeve 888 carried by housing 884 and extending horizontally through interior region 866. Ends of sleeve 888 are appended to respective outer and inner vertical walls 891, 899 of housing 884. Walls 891, 899 are each formed with an aperture 889 that communicates with an interior region of sleeve 888. Latch 886 extends through apertures 889 and sleeve 888 and engages a vertical back wall 890 of receptacle 840, as described in more detail below.

Outer vertical wall 891 of housing 884 and sleeve 888 cooperate to provide a monolithic unit that is coupled, such as by RF or ultrasonic welding or adhesive, to a main portion 892 of housing 884 (see FIGS. 20–23). An outer end portion 893 of sleeve 888 is formed monolithically with a recessed portion 894 of wall 891. Wall 891 has a peripheral flange 895 that is coupled to a corresponding peripheral flange 896 of main portion 892. An inner end portion 897 of sleeve 888 is coupled to a recessed portion 898 of inner vertical wall 899 of main portion 892. Outer wall 891 has inlet port 850 formed integrally therewith or appended thereto. Inner wall 899 has upper pressure port 852 and lower outlet port 857 formed integrally therewith or appended thereto.

Figure 21:
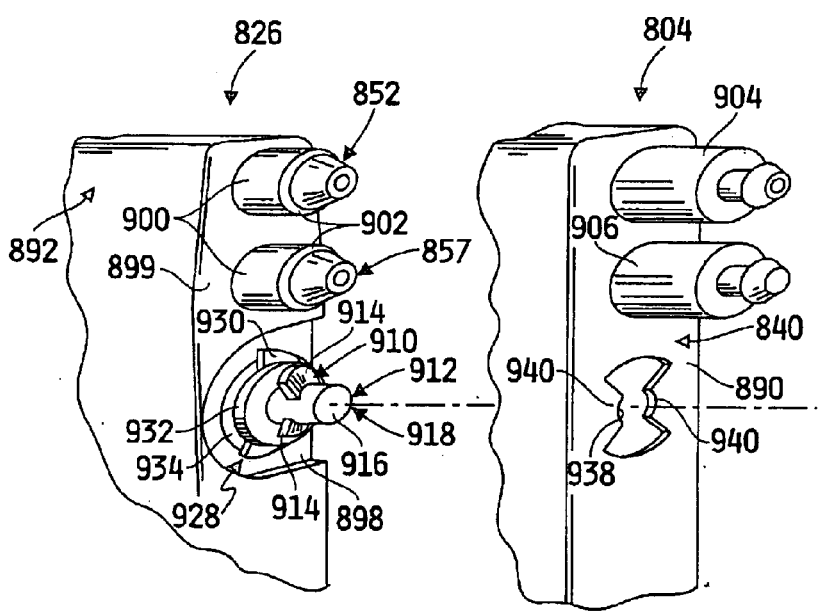
FIG. 21 is a fragmentary perspective view of a portion of the canister of FIG. 20 and a portion of a receptacle of the housing in which the canister is received.
Figure 22:
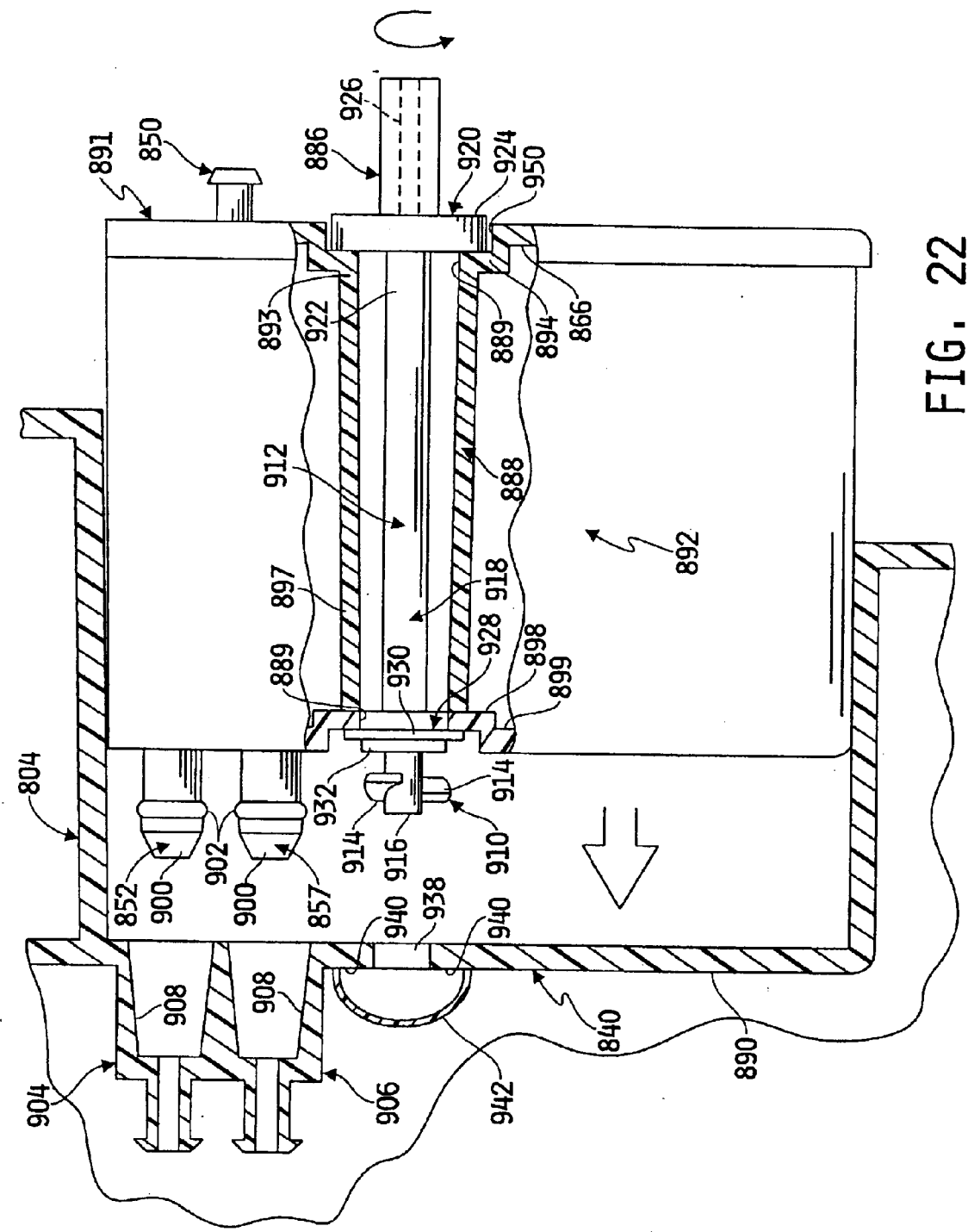
FIG. 22 is a side sectional view of the canister partially inserted into the receptacle.

Latch 886 has a fastener 910 to couple to back wall 890 and an actuator 912 to rotate fastener 910, as illustrated in FIGS. 21–23. Fastener 910 has a pair of bayonet-style canted lugs 914 coupled to an inner end portion 916 of a shaft 918 of actuator 912. Lugs 914 are diametrically opposed to one another and extend somewhat circumferentially and axially on shaft 918.

Actuator 912 further has a handle 920 coupled to an outer end portion 922 of shaft 918, as illustrated in FIGS. 14, 20, 22 and 23. Handle has a disk 924 coupled to end portion 922 and a flange 926 coupled to and extending radially outwardly from disk 924. Disk 924 and a portion of flange 926 are positioned within recessed portion 894. Recessed portion 894 has a pair of stop edges 952 (see FIG. 20) positioned to restrict rotation of flange 926 to about 90 degrees.

A retainer 928 (see FIGS. 21–23) is mounted to shaft 918 between handle 920 and fastener 910. Illustrative retainer 928 has a clip 930, such as an e-clip, and a clip mount 932. Clip mount 932 takes the form of a disk mounted to shaft 918 and has a circumferential groove 934 configured to receive clip 930. Disk 932 has a diameter smaller than the inner diameter of sleeve 888 to facilitate insertion of fastener 910 through sleeve 888 during assembly of canister 826. After insertion of fastener 910 through sleeve 888, clip 930 is positioned in groove 934 to engage recessed portion 898 to prevent latch 886 from inadvertently withdrawing from sleeve 888. An inner portion of disk 932 is received in one of apertures 889 and disk 924 is received in a space defined by an arcuate edge 950 (see FIGS. 20, 22, and 23) of wall 891 to support latch 886 for rotation relative to housing 884.

Figure 24:
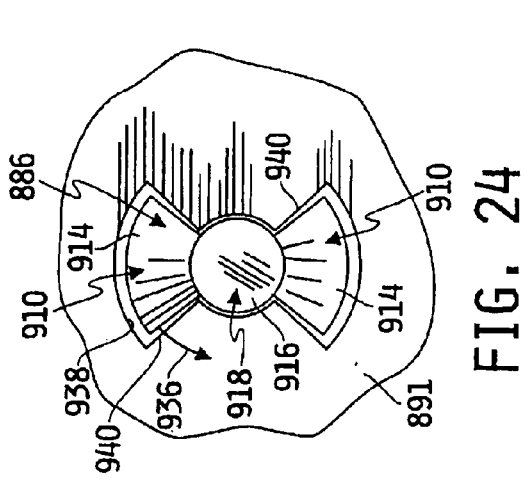
FIG. 24 is an enlarged elevation view of the interface between the latch and a wall of the receptacle showing lugs of the latch aligned with lug-receiving spaces of an aperture formed in the receptacle wall.
Figure 25:
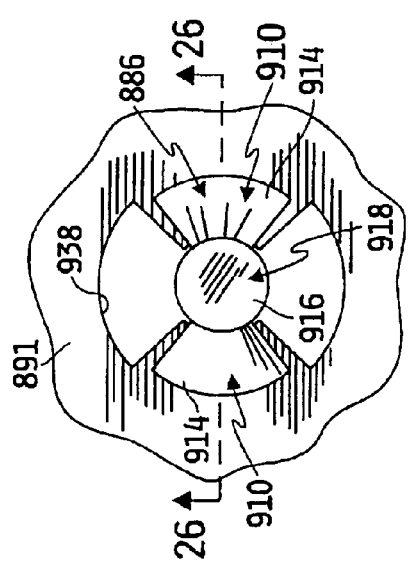
FIG. 25 is an enlarged elevation view, similar to FIG. 24, showing the lugs of the latch misaligned with the lug-receiving spaces of the aperture to retain the canister in the receptacle.
Figure 26:
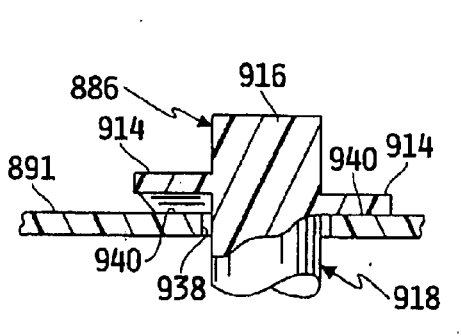
FIG. 26 is a sectional view taken along line 26—26 of FIG. 25 showing engagement between the lugs and the receptacle wall.
Figure 28:
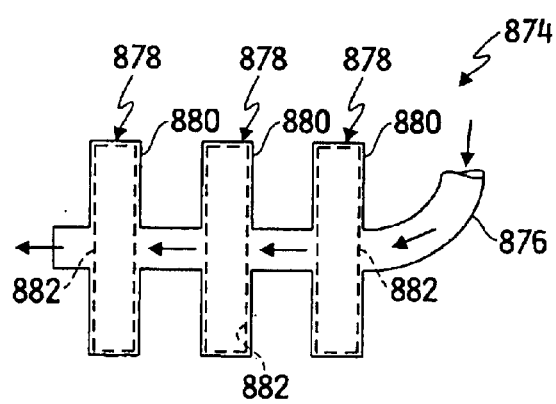
FIG. 28 is a diagrammatic view of a three-chambered muffler.

After latch 886 is coupled to housing 884, canister 826 is ready to be installed within receptacle 840. A caregiver places canister 826 within receptacle 840 (see FIG. 22) and inserts leading edges of lugs 914 through an aperture 938 of back wall 890 shaped to receive lugs 914 (see FIG. 24). The caregiver then rotates handle 920, and thus lugs 914, by hand, for example, approximately 90 degrees in a direction 936 (see FIG. 25). This rotation causes lugs 914 to cam against inwardly facing thrust surfaces 940 of back wall 890 (see FIG. 26) so that canister 826 moves toward back wall 890 and pressure port 852 and outlet port 857 are drawn into corresponding upper 904 and lower 906 sockets, respectively, of back wall 890 (see FIGS. 22–23). Each port 852, 857 has a nipple 900 that is inserted into the respective socket 904, 906 and an O-ring 902 surrounding nipple 900. When lugs 914 are rotated against surfaces 940, nipples 900 are drawn into sockets 904, 906 so that O-rings 902 sealingly engage tapered walls 908 of sockets 904, 906. Sockets 904, 906 provide portions of lines 854, 858, respectively. A dome cover 942 is positioned on an inner surface of back wall 890 and over lugs 914 and inner end portion 916 of shaft 918.

Canister 826 is removed from receptacle 840 and disposed of when canister 826 is full of waste material. To do so, a caregiver removes line 20 from inlet port 850, places a cap (not shown) on port 850 to prevent spillage, and rotates handle 920 in a reverse direction 944 to release lugs 914 from back wall 890. The caregiver then pulls on side grips 946 (see FIG. 14) of canister 826 to remove canister 826 from receptacle 840. As canister 826 is removed from receptacle 840, lugs 914 pass back through aperture 938 and pressure port 852 and outlet port 857 are withdrawn from upper and lower sockets 904, 906. Canister 826 can then be discarded and a new, empty canister 826 can be installed within receptacle 840.

By having latch 886 included as part of canister 826, which is disposed of after being filled with waste material, latch 886 is not used over and over again, thereby preventing lugs 914 from wearing down and degrading the sealed connection between ports 852, 857 and sockets 904, 906.

Figure 29:
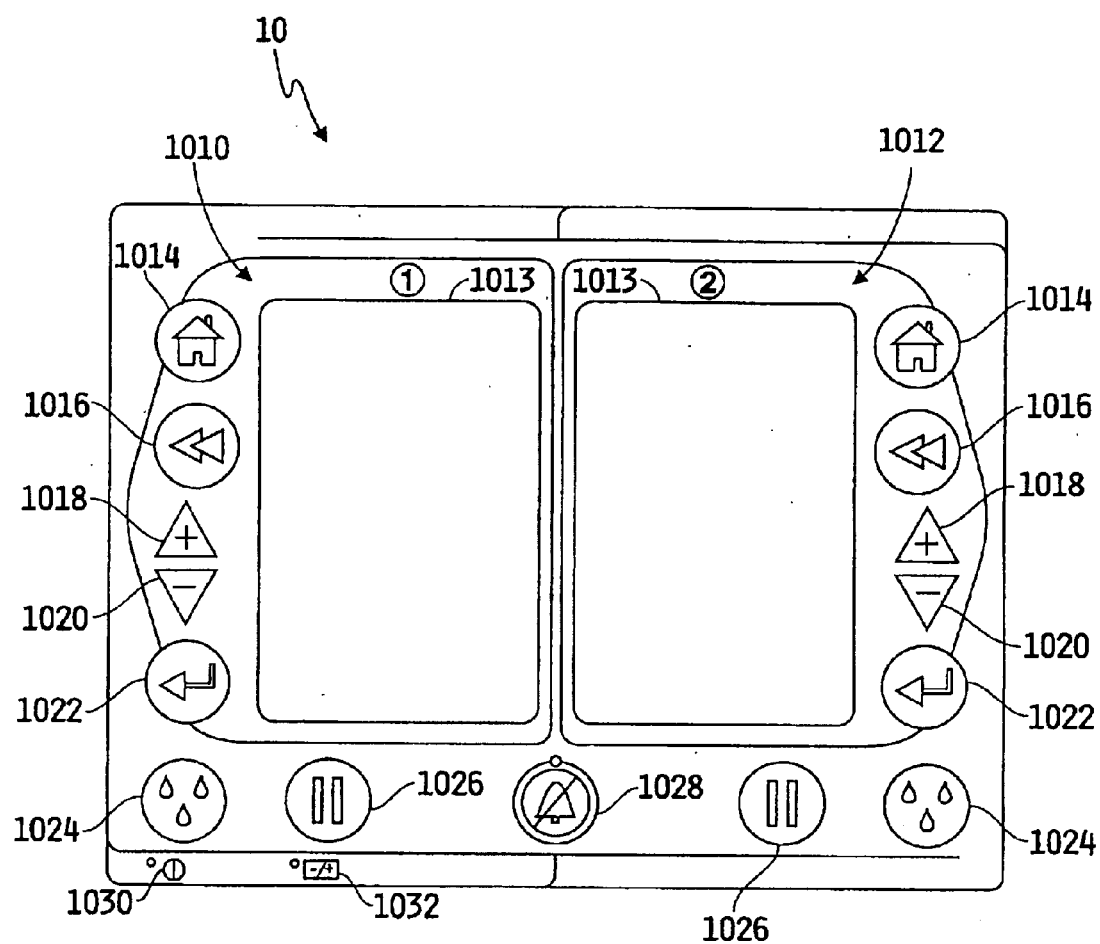
FIG. 29 is an elevational view of a user interface of the wound treatment apparatus of FIG. 14 showing the user interface having a left side which is associated with a first system for providing vacuum therapy to a first wound of a patient and a right side which is associated with a second system for providing vacuum therapy to a second wound of the patient, each side having a display and a plurality of user controls.

User interface 10 is shown, for example, in FIG. 29. Interface 10 is divided into a left side 1010 for operation of system 806 and a right side 1012 for operation of system 808. Each side 1010, 1012 has an electronic display 1013 to display various screens and a plurality of user input controls to control operation of the respective system 806, 808. Each display 1013 includes, for example, a liquid crystal display (LCD) and backlighting provided by a column of LED's behind the LCD. The user controls include a home control or button 1014 to go to a home screen 1015 (see FIG. 35) and a back control or button 1016 to navigate to a previous screen until the home screen is reached. The user controls also include up control or button 1018 and down control or button 1020 for purposes described herein, an enter button 1022 to make various selections, a flush or irrigation control or button 1024 to operate the irrigation mechanism discussed herein with respect to apparatus 2, 802 and a pause control or button 1026 to suspend operation of the respective vacuum source 110.

One of the user controls is an alarm silence control or button 1028. Button 1028 is common to both systems 806, 808 to silence all audible alarms of control unit 803 for a predetermined period of time, such as fifteen minutes. An LED illuminates button 1028 when button 1028 is pressed to indicate that all the audible alarms have been silenced. Pressing button 1028 again at any time during the predetermined time period starts the predetermined time period over. It should be appreciated that the identified functions of buttons 1014, 1016, 1018, 1020, 1022, 1024, 1026, 1028 are exemplary and that buttons 1014, 1016, 1018, 1020, 1022, 1024, 1026, 1028 can be operated to provide other functions as well.

Interface 10 also has a power LED 1030 and a battery LED 1032. Power LED 1030 provides a visual indication when control unit 803 is powered on. Control unit 803 is powered on and off by a rocker switch (not shown). Battery LED 1032 provides a visual indication when control unit 803 is using power from battery 954.

Control unit 803 is configured to operate in a power-saving mode after a predetermined period of time of inactivity. During this power-saving mode, the backlighting of displays 1013 is extinguished. Pressing any of buttons 1014, 1016, 1018, 1020, 1022, 1024, 1026, 1028 during the power-saving mode deactivates the power-saving mode and turns the backlighting back on. An alarm condition automatically deactivates the power-saving mode.

Figure 30:
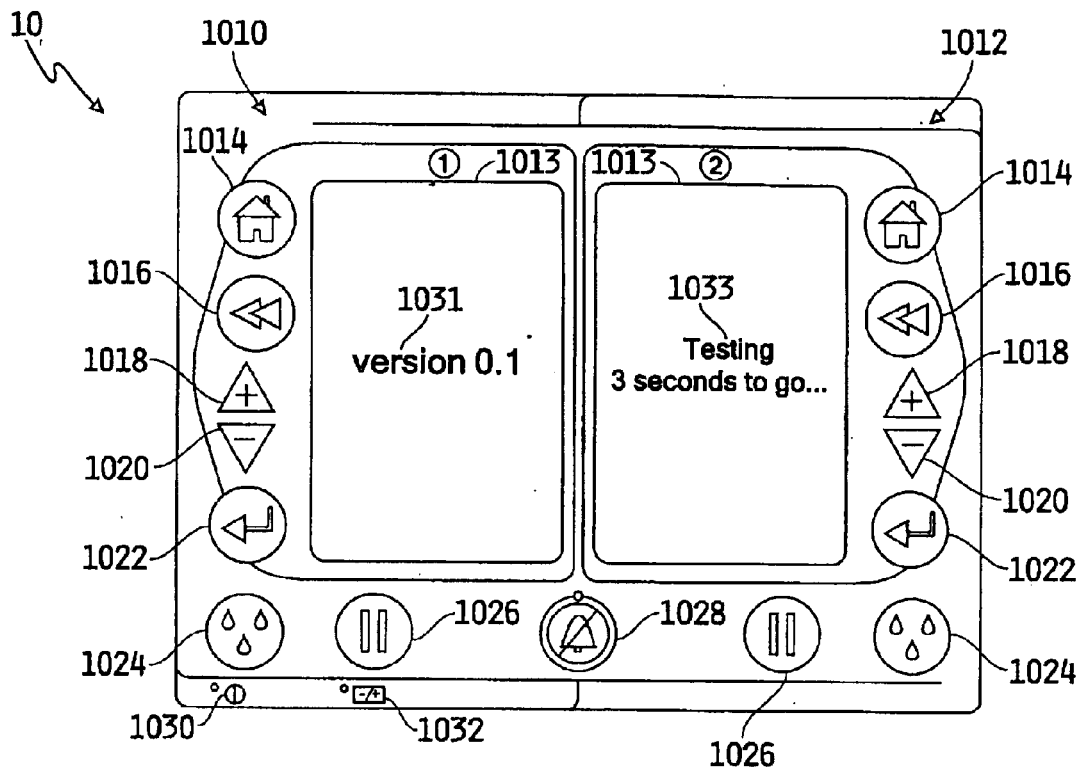
FIG. 30 is an elevational view of the user interface showing a software revision level on the left display and the number of seconds remaining to complete a system self-test on the right display.

Referring to FIG. 30, control unit 803 conducts a Power On Self Test (POST) when control unit 803 is powered on initially. During the POST, text 1031 appears on one of displays 1013 indicating the revision level of the software of controller 850 and a countdown 1033 appears on the other display 1013 indicating the approximate time remaining to complete the POST.

Figure 31:
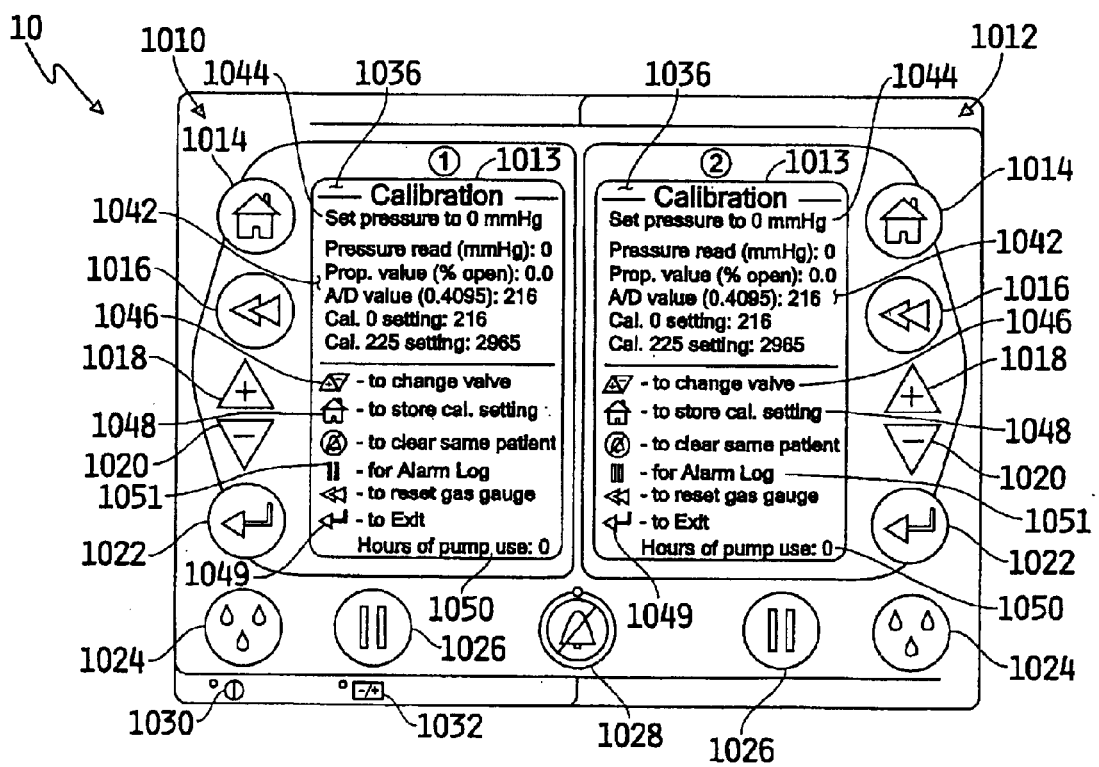
FIG. 31 is an elevational view of the user interface showing a calibration screen on the left and right displays to calibrate pressure sensors of the wound treatment apparatus.

During countdown 1033, a user, such as a service technician, can transition control unit 803 to a calibration mode to calibrate pressure sensors 124. To make this transition, the user presses both pause buttons 1026 simultaneously during countdown 1033 to cause a calibration screen 1036, as shown in FIG. 31, to appear on both displays 1013. Each calibration screen 1036 is associated with one of vacuum sources 110.

Once at calibration screen 1036, the user can calibrate one or both pressure sensors 124. When control unit 803 is powered on, both vacuum sources 110 automatically begin to operate and both proportional valves 130 are fully closed. Vacuum sources 110 continue to operate and valves 130 remain in their fully closed position when the calibration mode begins. Since the procedure for calibrating pressure sensors 124 is the same for both pressure sensors 124, the calibration procedure is described for only one of them.

In general, two outputs of pressure sensor 124 are correlated to two calibration pressures to calibrate pressure sensor 124. In one embodiment, the first calibration pressure is, for example, 0 millimeters of Mercury (or 0 mm Hg, i.e., atmospheric pressure) and the second calibration pressure is, for example, 225 mm Hg of negative pressure.

Figure 32:
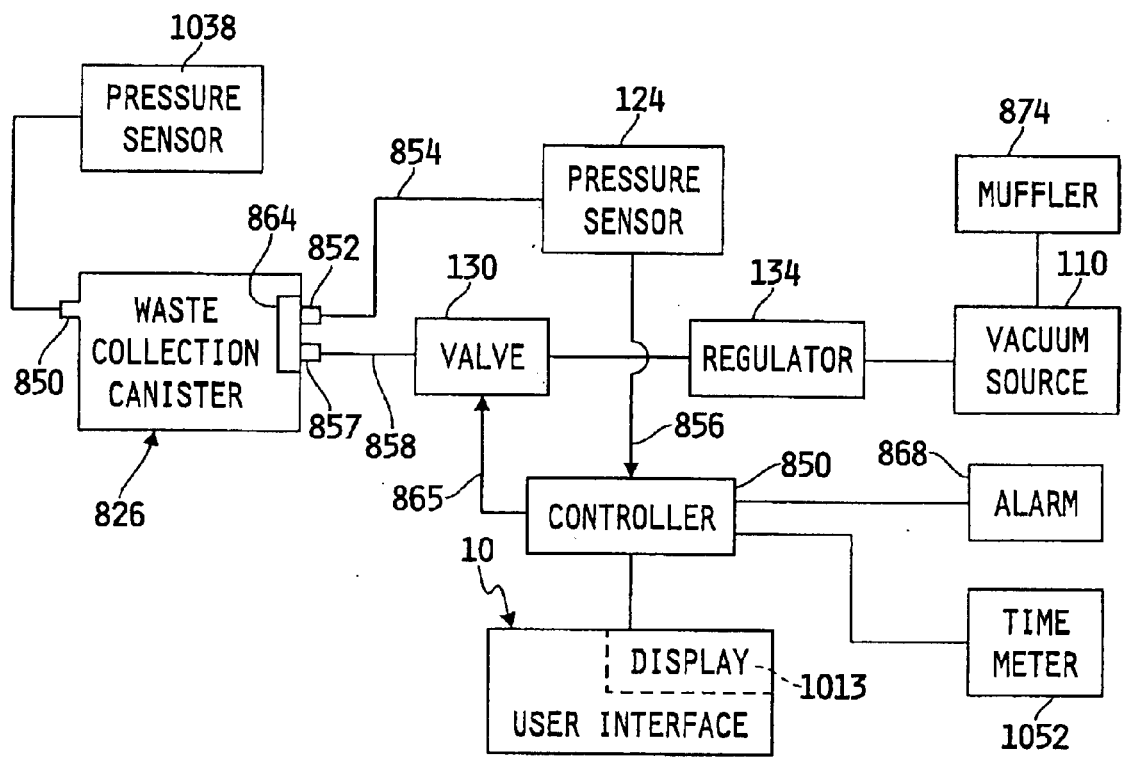
FIG. 32 is a diagrammatic view of components of one of the two systems of the wound treatment apparatus showing a pressure sensor coupled to a left inlet port of a waste collection canister to calibrate a pressure sensor coupled to a right pressure port of the waste collection canister.

To obtain the first output of pressure sensor 124, a pressure sensor 1038, such as a manometer, is positioned in communication with interior region 866 of canister 826, as shown diagrammatically in FIG. 32. In particular, sensor 1038 is coupled to inlet port 850 so that sensor 1038 communicates with the pressure in interior region 866. Sensor 124 is already positioned in communication with the pressure of interior region 866 since sensor 124 is coupled to pressure port 852.

Valve 130 remains fully closed when control unit 803 enters the calibration mode. Being fully closed, valve 130 blocks communication between vacuum source 110 and interior region 866 so that atmospheric pressure is established in interior region 866. Sensors 124, 1038 thus communicate with atmospheric pressure at the beginning of the calibration process.

When a user observes that sensor 1038 indicates the first calibration pressure, the user operates a user control to store the output of sensor 124 in controller 850 and thereby correlate that output to the first calibration pressure. For example, when the user observes that sensor 1038 indicates a first calibration pressure of 0 mm Hg, the user presses home button 1014 to store the corresponding analog-to-digital (A/D) output of sensor 124 in controller 850 as a first calibration setting and thereby correlate that output to 0 mm Hg (pressing home button 1014 in this instance does not cause home screen 1015 to appear). Illustratively, the A/D output of sensor 124 can range from 0 to 4095.

The user then proceeds to correlate a second output from sensor 124 with the second calibration pressure. Sensors 124, 1038 remain coupled to ports 852, 850, respectively, and the user operates up and down buttons 1018, 1020 as necessary to establish the second calibration pressure in interior region 866 to cause sensors 124, 1038 to communicate with the second calibration pressure. In general, in the calibration mode, pressing up button 1018 raises the pressure in interior region 866 (i.e., makes the pressure more positive) by moving valve 130 toward its fully closed position so that vacuum source 110 establishes less negative pressure in interior region 866. On the other hand, pressing down button 1020 lowers the pressure in interior region 866 (i.e., makes the pressure more negative) by moving valve 130 toward its fully opened position so that vacuum source 110 establishes more negative pressure in interior region 866. To provide a second calibration pressure of 225 mm Hg of negative pressure in interior region 866, valve 130 is opened somewhat to permit communication between vacuum source 110 and interior region 866.

When the user observes that sensor 1038 indicates the second calibration pressure, the user again operates a control to correlate the output of sensor 124 with the second calibration pressure. For example, when the user observes sensor 1038 indicate a second calibration pressure of 225 mm Hg of negative pressure, the user again presses home button 1014 to store the corresponding A/D output of sensor 124 in controller 850 as a second calibration setting and thereby correlate that output of sensor 124 with 225 mm Hg of negative pressure. The calibration process is completed once the second calibration setting is obtained. Controller 850 then uses the first and second calibration settings to control vacuum source 110 to provide a desired pressure from the entire range of possible pressures in canisters 826.

Calibration screen 1036 provides calibration information for the user. Calibration screen 1036 has text 1042 providing the current pressure reading in mm Hg of sensor 124, the percentage that valve 130 is open, the A/D output of sensor 124, the first calibration setting, and the second calibration setting.

Calibration screen 1036 also provides calibration information to instruct a user when control unit 803 is in the calibration mode. Information 1044 at the top of calibration screen 1036 instructs the user to set the pressure to 0 mm Hg at the beginning of the calibration process. Information 1046 indicates that up and down buttons 1018, 1020 can be operated to change the position of valve 130. Information 1048 indicates that home button 1014 can be operated to store the calibration settings. Information 1049 provides that the calibration mode can be exited by pressing enter button 1022.

Control unit 803 has a time meter 1052 (see FIG. 27) associated with each vacuum source 110 to keep track of how long the associated vacuum source 110 has operated. Based on the operation of time meter 1052, a value indicative of how long vacuum source 110 has operated is stored in a memory location of controller 850. The value indicative of how long vacuum source 110 has operated is updated by controller 850 and is displayed during calibration of controller 850. Each calibration screen 1036 displays the total number of hours of use of the associated vacuum source 110 in line of text 1050.

Figure 33:
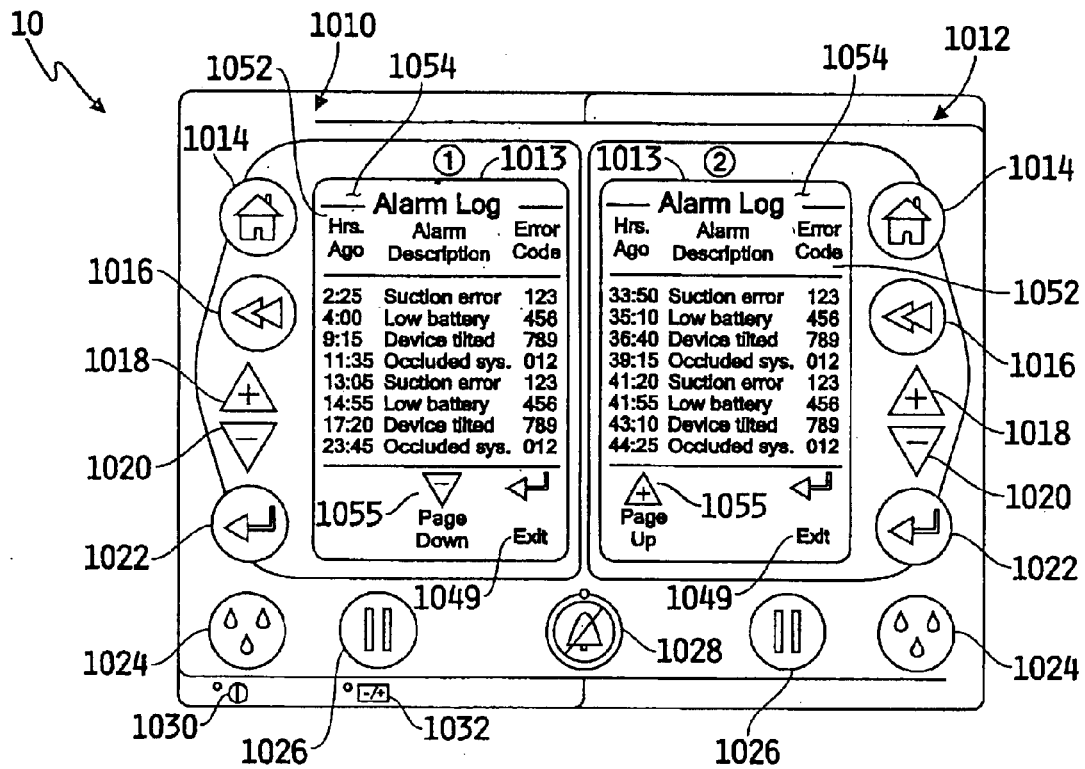
FIG. 33 is an elevational view of the user interface showing alarm logs providing information associated with activations of alarms of the wound treatment apparatus.

As indicated by text 1051 (see FIG. 31), an alarm log 1052 (see FIG. 33) associated with each alarm 868 is accessed by pressing the associated pause button 1026 in calibration screen 1036. When pause button 1026 on left side 1010 is pressed in the calibration screen 1036, display 1013 on left side 1010 displays an alarm log screen 1054 having an alarm log 1052 associated with alarm 868 of system 806. When pause button 1026 on right side 1010 is pressed in the calibration screen 1036, display 1013 on right side 1010 displays alarm log screen 1054 having alarm log 1052 associated with alarm 868 of system 808. Each alarm log 1052 lists all activations of the associated alarm 868 occurring within the previous 48 hours and provides information regarding the alarm activations including how long ago the activations occurred, descriptions of the activations, and error codes associated with the activations.

Alarm log screen 1054 provides navigation information for a user at the bottom of the screen. Exit information 1049 instructs that pressing enter button 1022 will cause the respective display 1013 to exit the alarm log screen 1054. Display 1013 returns to calibration screen 1036 when alarm log screen 1054 is exited. Page down/page up information 1055 instructs that pressing down button 1020 will cause the associated display 1013 to display the next page of alarm log 1052 and pressing up button 1018 will cause the associated display 1013 to display the previous alarm log 1052.

Figure 34:
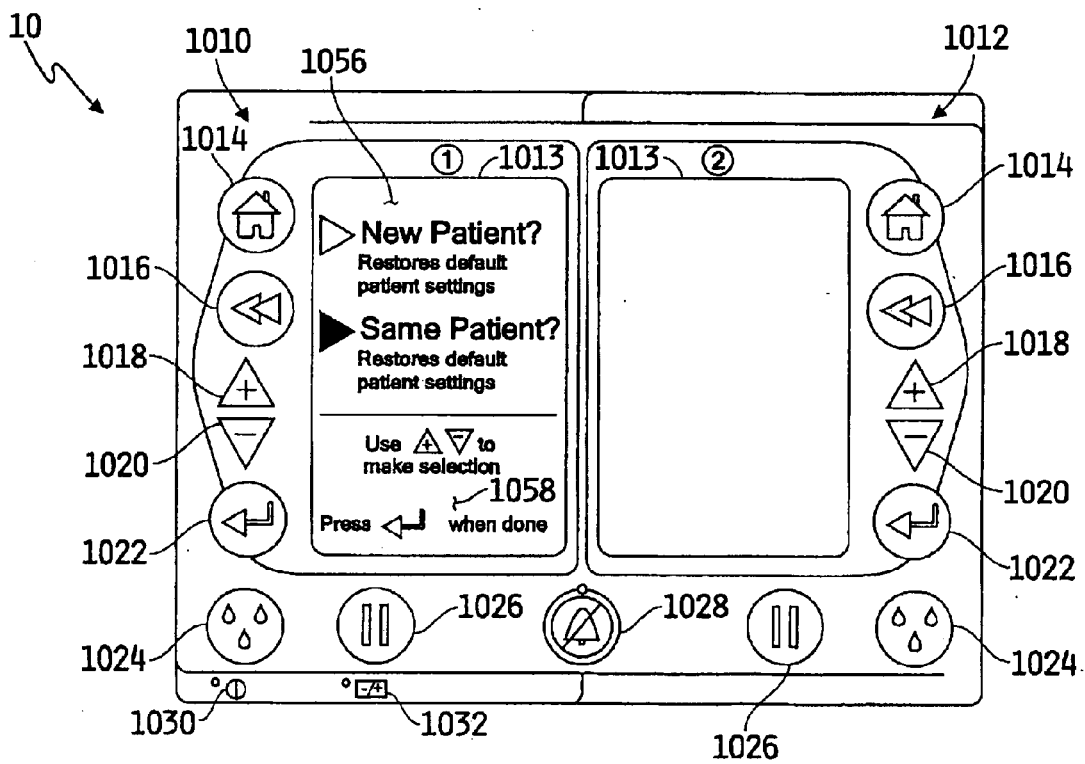
FIG. 34 is an elevational view of the user interface showing a screen in which a user is prompted to select whether the next application of the wound treatment apparatus will be for a new patient or for the same patient as the most previous application of the wound treatment apparatus.

When calibration screen 1036 is exited, a patient settings screen 1056 appears on one of displays 1013, as shown in FIG. 34. The user is prompted to select whether control unit 803 will be used for a "New Patient" or the "Same Patient" (i.e., the most recent patient for which the system was used). Selecting "New Patient" restores the system default settings and allows the user to select new patient settings. Selecting "Same Patient" causes the system to retain the most recently stored patient settings. Patient settings screen 1056 provides information 1058 at the bottom of the screen instructing that up and down buttons 1018, 1020 can be used to toggle between the "New Patient" and "Same Patient" options and instructing the user to press enter button 1022 when the user has made a selection. Pressing enter button 1022 when the "New Patient" option is selected causes home screen 1015, shown, for example, in FIG. 35, to appear on display 1013 to allow the user to select new patient settings. If the "Same Patient" option is selected when enter button 1022 is pressed, the most recently stored patient settings will be accepted and control unit 803 will be ready for wound therapy.

Figure 35:
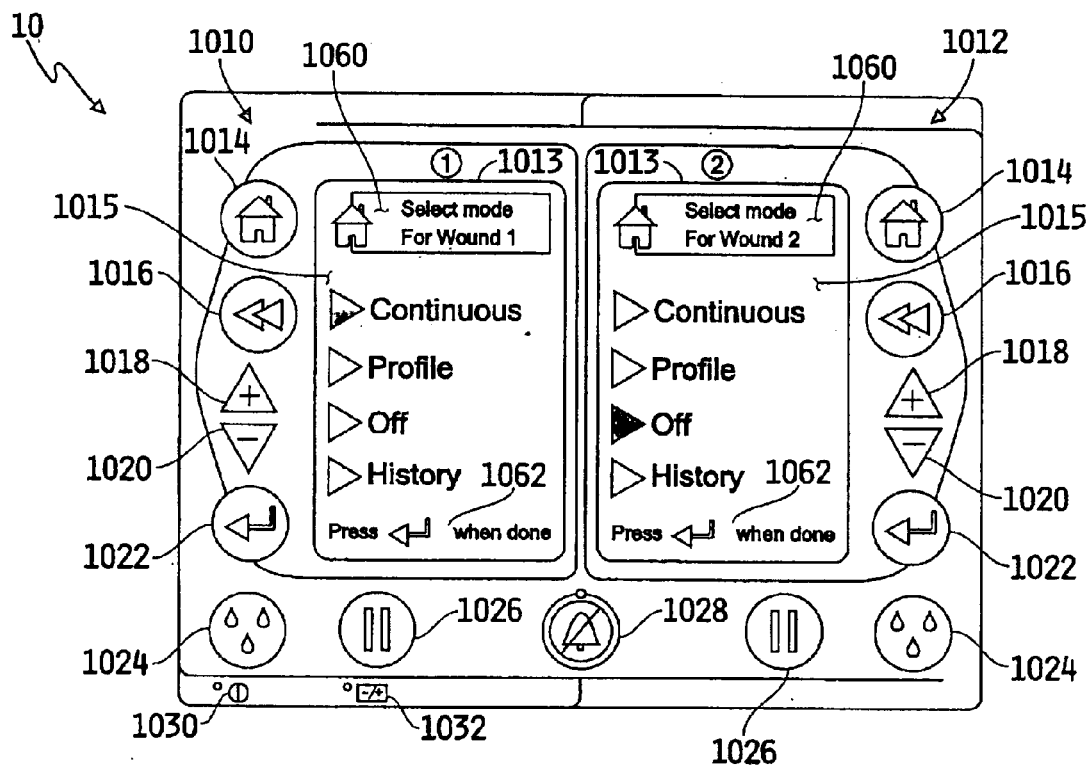
FIG. 35 is an elevational view of the user interface showing the left and right displays prompting a user to select one of four modes of operation for the associated systems of the wound treatment apparatus.

In home screen 1015, information 1060 at the top of the screen instructs the user to select one of four modes for system 806 and system 808, as shown in FIG. 35. The four modes are labeled as "Continuous," "Profile," "Off," and "History," each of which is explained in more detail below. By default, the Continuous mode is selected for system 806 on left side 1010 and the Off mode is selected for system 808 on right side 1012. By pressing up and down buttons 1018, 1020, the user can toggle between the four modes to select any one of them. Information 1062 at the bottom of home screen 1015 instructs the user to press enter button 1022 when the user has selected one of the four modes for the respective system 806, 808 to confirm the selection.

Figure 36:
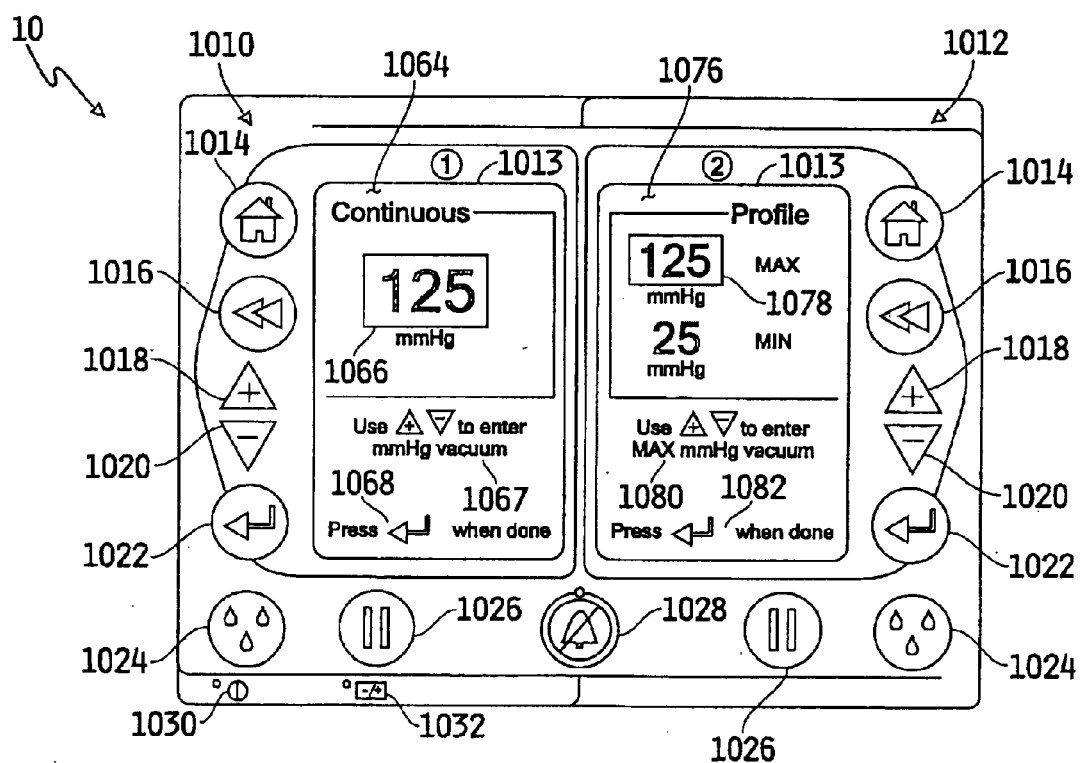
FIG. 36 is an elevational view of the user interface showing the system associated with the left display operating in a Continuous mode and prompting a user to enter a desired negative pressure to be applied to the first wound and showing the system associated with the right display operating in a Profile mode and prompting the user to enter a maximum negative pressure that can be applied to the second wound.

In Continuous mode, the user can select a desired negative pressure setting to be applied to the respective wound 16 by the respective system 806, 808. Selection of Continuous mode in home screen 1015 causes a first continuous mode screen 1064 to appear on the respective display 1013, as shown with respect to display 1013 on left side 1010 in FIG. 36. The default desired negative pressure setting of 125 mm Hg for the respective vacuum source 110 appears in flashing text 1066 in screen 1064. The user can change the desired negative pressure setting by pressing up and down buttons 1018, 1020, as indicated by information 1067 displayed on screen 1064. The desired negative pressure setting can be increased or decreased within a range of 25 mm Hg to 175 mm Hg in 10 mm Hg increments. Pressing enter button 1022 will accept the new desired negative pressure setting and initiate operation of the respective vacuum source 110 for wound therapy.

Once wound therapy begins, the respective system 806, 808 remains in continuous mode and a second continuous mode screen 1070 (see FIG. 37) appears on the respective display 1013. Screen 1070 provides the current desired negative pressure setting 1071, information 1072 indicating that the user can go back to first continuous mode screen 1064 by pressing button 1016 to change the desired negative pressure setting, and information 1074 indicating that the user can go to home screen 1015 by pressing home button 1014.

In Profile mode, the user can select the maximum and minimum negative pressure settings that the respective system 806, 808 can apply to the respective wound 16. Selection of the Profile mode in home screen 1015 causes a first profile mode screen 1076 to appear on the respective display 1013, as shown with respect to display 1013 on right side 1012 in FIG. 36. The default maximum and minimum negative pressure settings of 125 mm Hg and 25 mm Hg, respectively, appear on screen 1076 with the maximum negative pressure setting appearing in flashing text 1078. The user can change the maximum negative pressure setting by increments of 10 mm Hg by pressing up and down buttons 1018, 1020, as indicated by information 1080 displayed on screen 1076. Pressing enter button 1022 will accept the maximum negative pressure setting on screen 1076, as indicated by information 1082, and cause a second profile mode screen 1083 to appear on display 1013.

Figure 37:
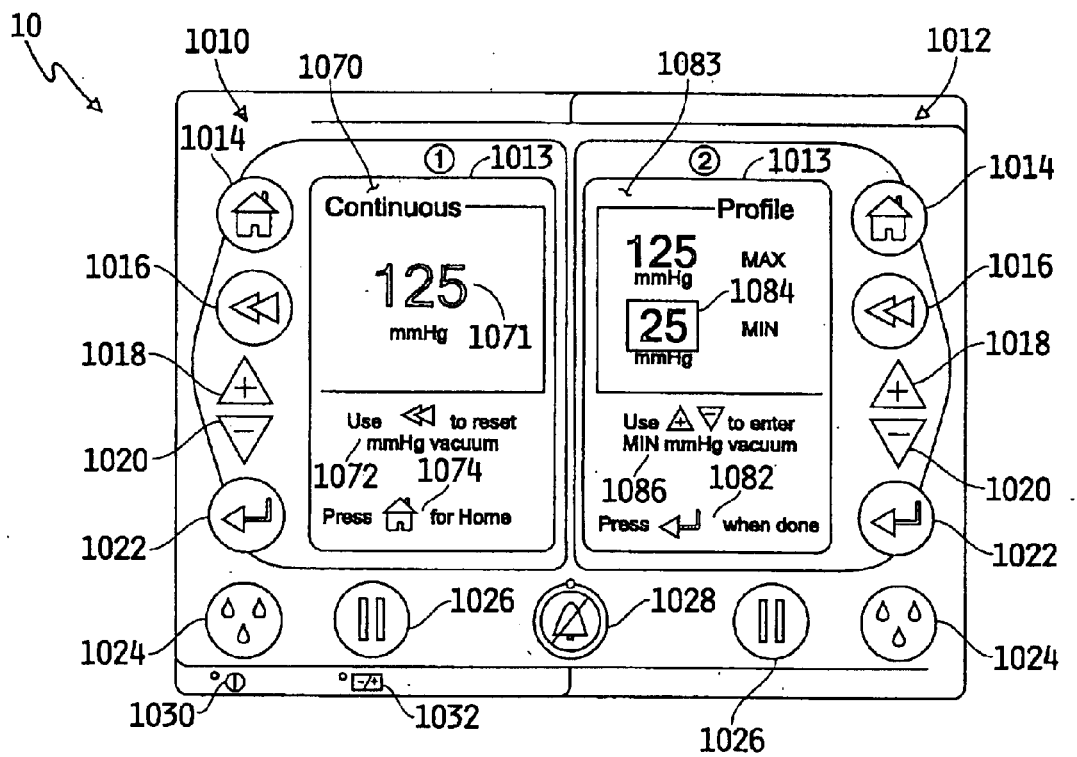
FIG. 37 is an elevational view of the user interface showing the system associated with the left display operating normally in Continuous mode and showing the system associated with the right display operating in Profile mode and prompting the user to enter a minimum negative pressure that can be applied to the second wound.
Figure 38:
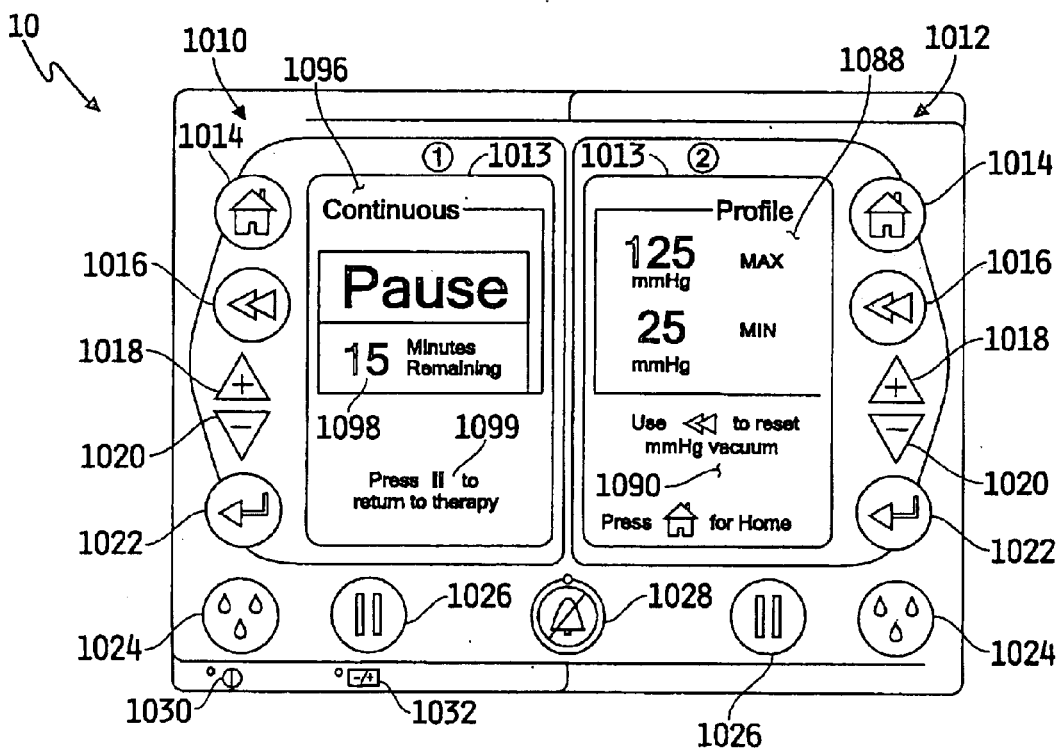
FIG. 38 is an elevational view of the user interface showing operation of the system associated with the left display paused for a period of time and showing the system associated with the right display operating normally in the Profile mode.

In second profile mode screen 1083, the minimum negative pressure setting appears in flashing text 1084 (see FIG. 37). As with the maximum negative pressure setting, the user can change the minimum negative pressure setting by increments of 10 mm Hg by pressing up and down buttons 1018, 1020, as indicated by information 1086 on screen 1083. Pressing enter button 1022 will accept the minimum negative pressure setting on screen 1084, as indicated by information 1082. Once the maximum and minimum negative pressure settings are selected, the respective system 806, 808 is ready for wound therapy and a third profile mode screen 1088 (see FIG. 38) appears on the respective display 1013. In screen 1088, the maximum and minimum negative pressure settings are displayed and information 1090 is provided to inform the user that pressing back button 1016 will allow the desired negative pressure setting to be changed and pressing home button 1014 will cause home screen 1015 to appear.

Pressing pause button 1026 suspends operation of the respective vacuum source 110 during Continuous or Profile mode for a predetermined time period, such as 15 minutes. A pause screen 1096 appears on the respective display 1013 when a user presses the pause button 1026 associated with that display 1013, as shown with respect to display 1013 on left side 1010 in FIG. 38. Text 1098 appears in pause screen 1096 to provide the number of minutes remaining during the pause period. Information 1099 is provided at the bottom of pause screen 1096 providing that pressing pause button 1026 again will end the pause period and resume the previous activity.

Selection of Off mode at home screen 1015 causes operation of the respective system 806, 808 to be suspended. An off mode screen 1088 (see FIG. 40) appears on the respective display 1013 during Off mode and information 1089 at the bottom of screen 1088 indicates that pressing home button 1014 will cause home screen 1015 to reappear.

Figure 39:
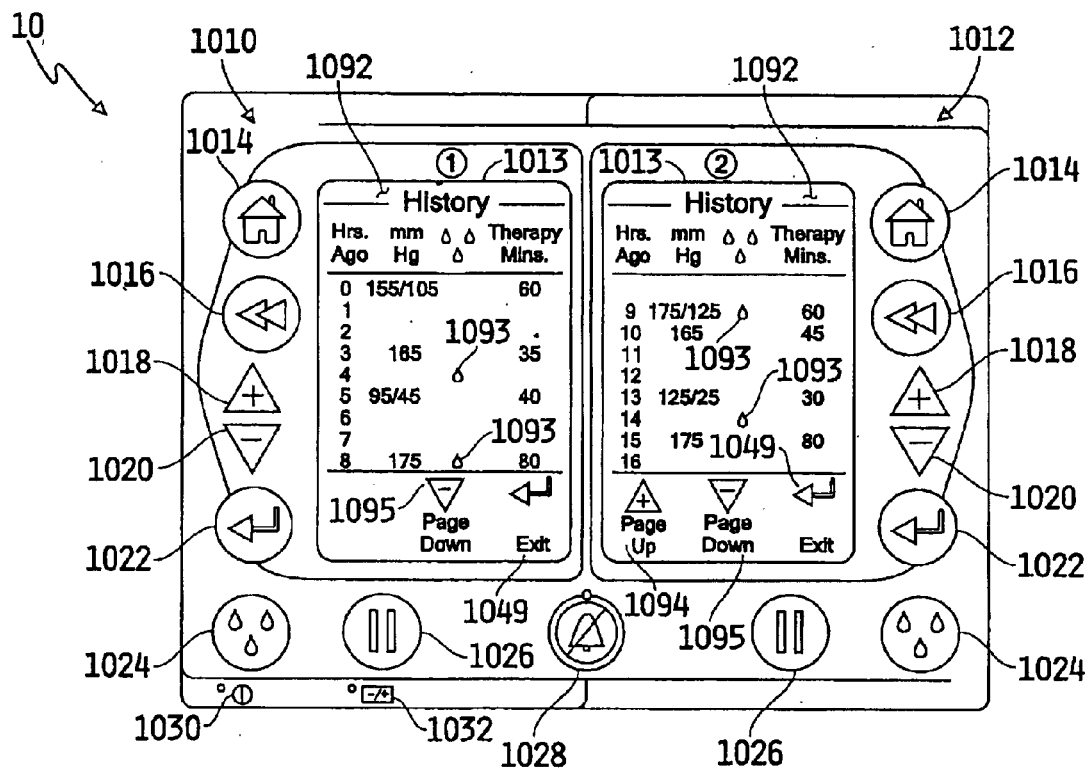
FIG. 39 is an elevational view of the user interface showing each display providing a record of activity of the associated system which is operating in a History mode.
Figure 40:
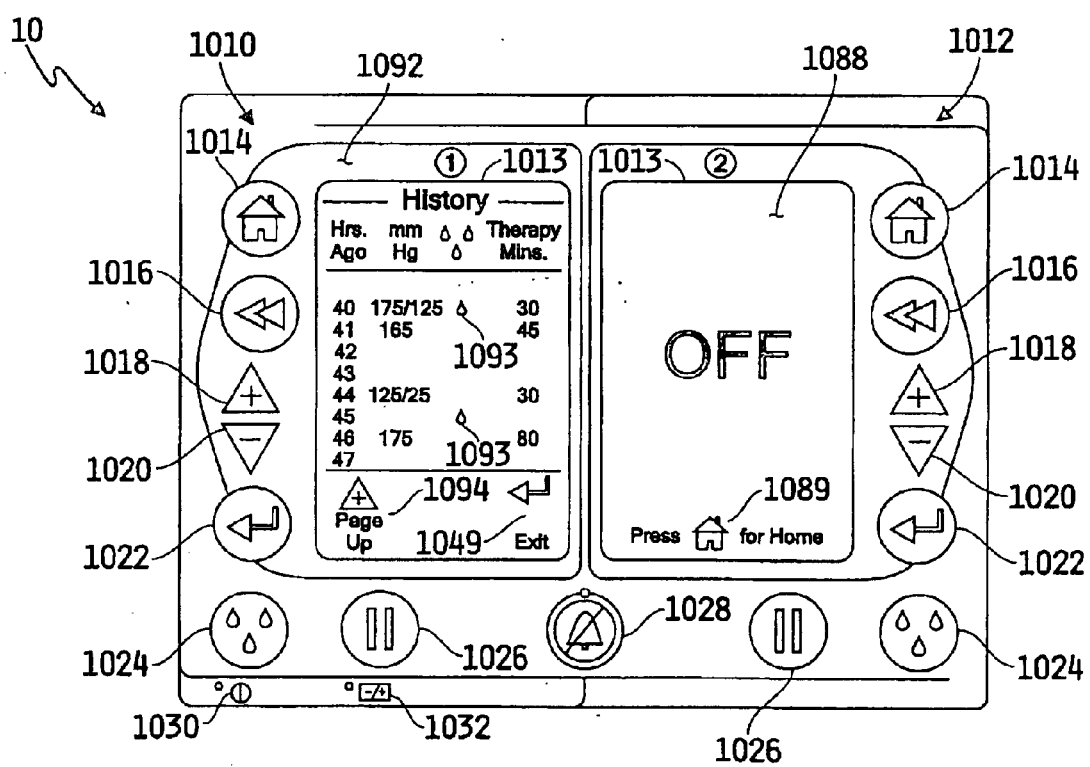
FIG. 40 is an elevational view of the user interface showing the system associated with the left display operating in History mode and the system associated with the right display operating an Off mode in which activity of that system is suspended.

Selection of History mode at home screen 1015 causes a history screen 1092 to appear on the respective display 1013, as shown in FIGS. 39 and 40. Screen 1092 provides history information relating to activity of the respective system 806, 808 for the previous 48 hours in which control unit 803 was powered on. In particular, the history information includes in table format the negative pressure settings associated with the respective mode (i.e., Continuous, Profile, Off) occurring at the end of each of the 48 hours, whether the respective irrigation mechanism was activated during the respective hour (as indicated by a liquid drop symbol 1093), and the number of minutes that the respective system 806, 808 provided wound therapy during the respective hour. Exit information 1049 is provided at the bottom of screen 1092 to instruct a user that History mode can be exited by pressing enter button 1022. One or both of information 1094 and information 1095 are also provided at the bottom of screen 1092 to instruct a user that up and down buttons 1018, 1020 can be operated to move between pages in History mode.

Figure 41:
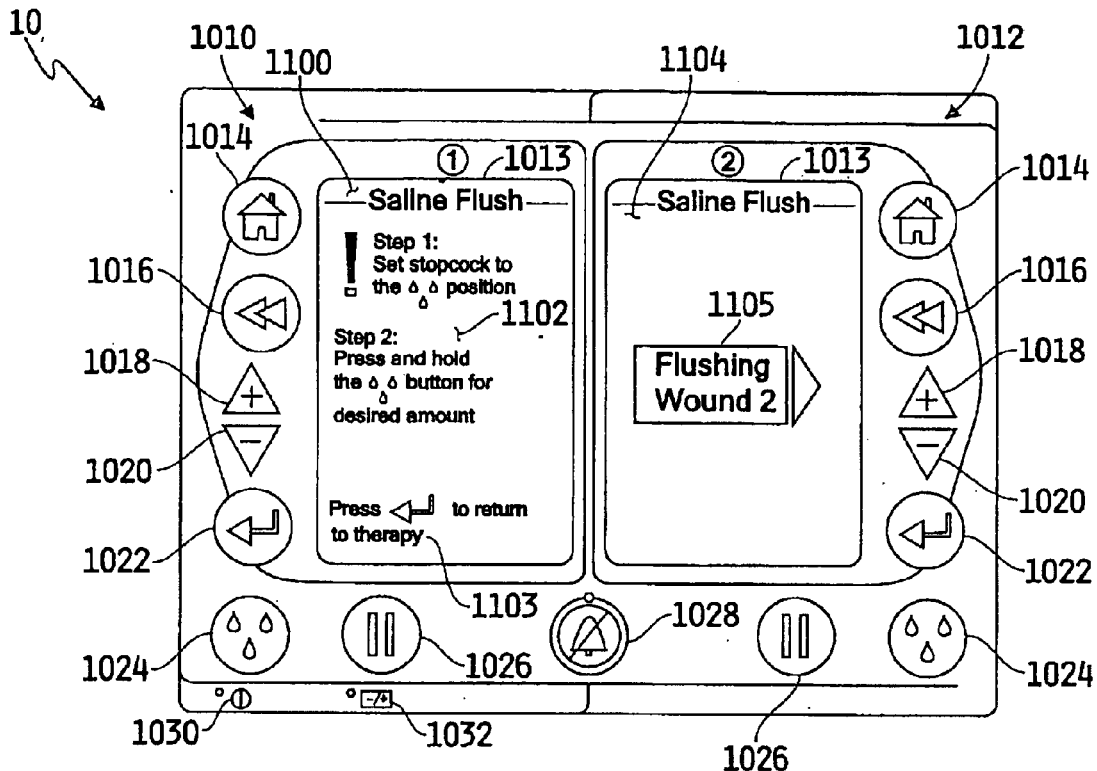
FIG. 41 is an elevational view of the user interface showing the left and right displays providing information for operating respective flush or irrigation mechanisms of the wound treatment apparatus.

Pressing irrigation button 1024 while the respective system 806, 808 is in the Continuous, Profile, or Off mode causes a flush start screen 1100 (see FIG. 41) to appear on the respective display 1013. Screen 1100 provides irrigation information 1102 instructing a user how to use the respective irrigation mechanism. Information 1102 instructs the user to set a switch or stopcock 1101 (see FIGS. 1 and 14) associated with the irrigation mechanism to a flush position to place the respective vacuum wound bandage 14, and thus the respective wound 16, in communication with the respective syringe 24. Information 1102 next instructs the user to press and hold irrigation button 1024 to operate the irrigation mechanism for irrigation of the respective wound 16. Information 1103 provides that pressing the respective enter button 1022 will end the irrigation procedure to reinitiate vacuum therapy.

Irrigation button 1024 is a momentary switch so that irrigation occurs only when irrigation button 1024 is pressed. When irrigation button 1024 is pressed for irrigation, a flush active screen 1104 (see FIG. 41) appears on one of displays 1013 with flashing text 1105 to indicate that the respective wound 16 is being irrigated or flushed.

Figure 42:
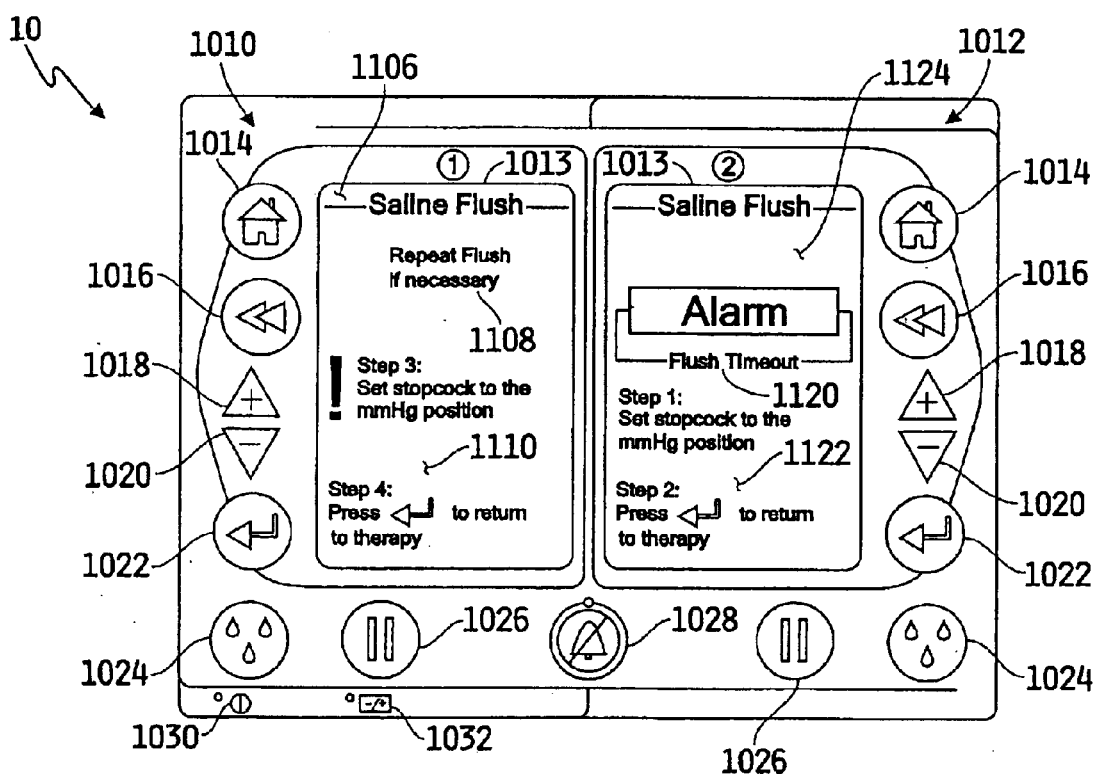
FIG. 42 is an elevational view of the user interface showing the left display providing information for operating the respective irrigation mechanism and the right display providing information associated with an alarm condition.

When irrigation button 1024 is released, a flush finish screen 1106 appears, as shown in FIG. 42. Screen 1106 provides information 1108 at the top thereof to indicate that the user can press irrigation button 1024 again to provide more irrigation. Screen 1106 also provides information 1110 instructing the user what to do if irrigation is completed. Information 1110 instructs the user to switch stopcock 1101 back to the vacuum position to place the respective vacuum wound bandage 14, and thus the respective wound 16, in communication with the respective vacuum source 110 and then to press enter button 1022 to end the irrigation procedure to reinitiate vacuum therapy. Flush screens 1100, 1104, 1106 cooperate to provide a flush or irrigation menu.

Controller 850 is configured to cause displays 1013 to display messages relating to three types of alarm conditions. Those alarm conditions can be referred to as a Reminder condition, an Alarm condition, and a Service Required condition, each of which is discussed in turn. Such alarm conditions are deviations from normal operation of the respective system 806, 808.

Figure 43:
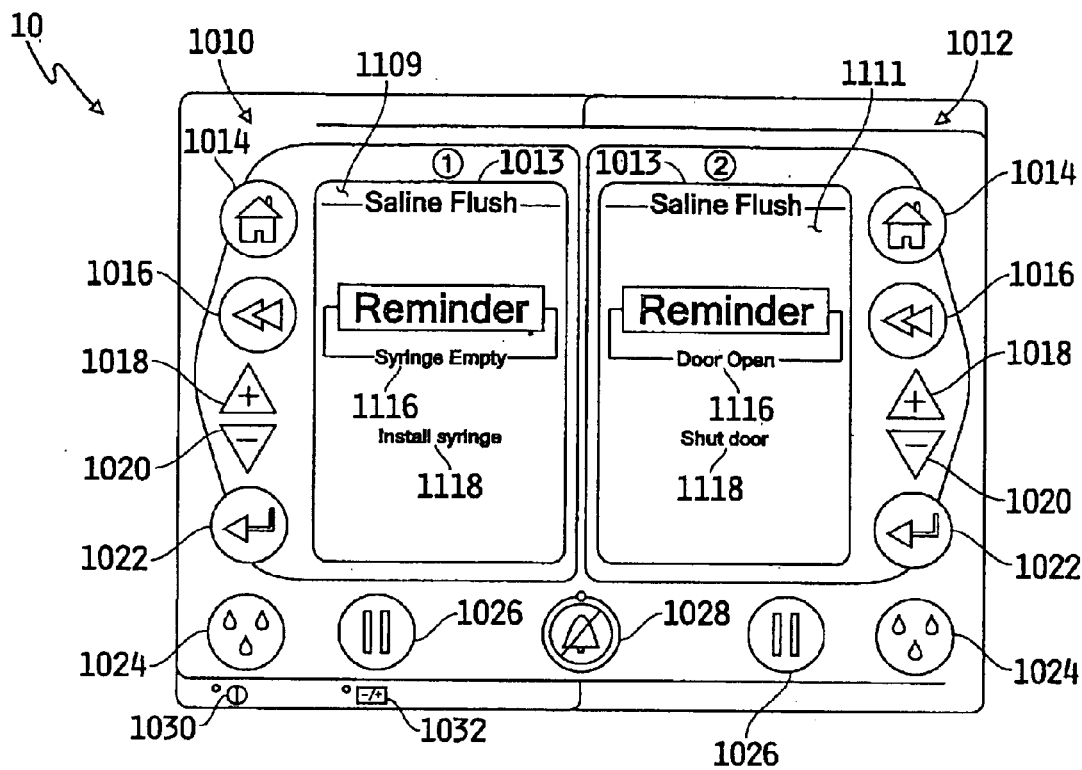
FIGS. 43–48 are elevational views of the user interface showing the left and right displays providing information associated with various alarm conditions.
Figure 44:
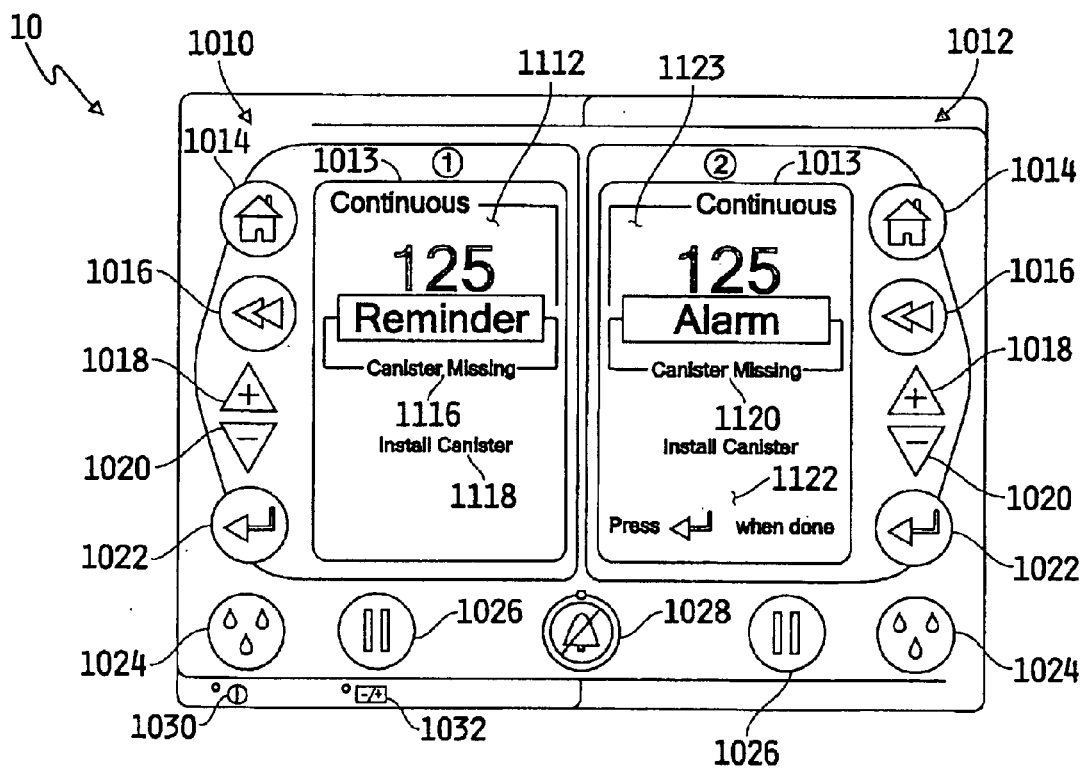
Figure 45:
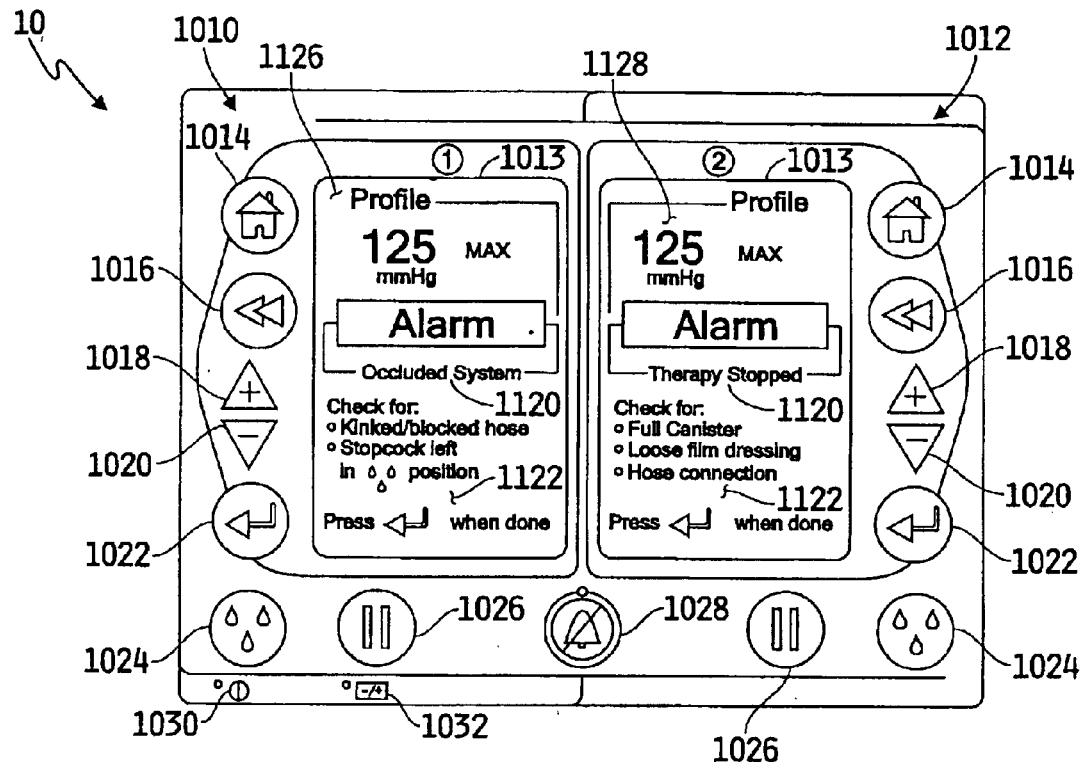
Figure 46:
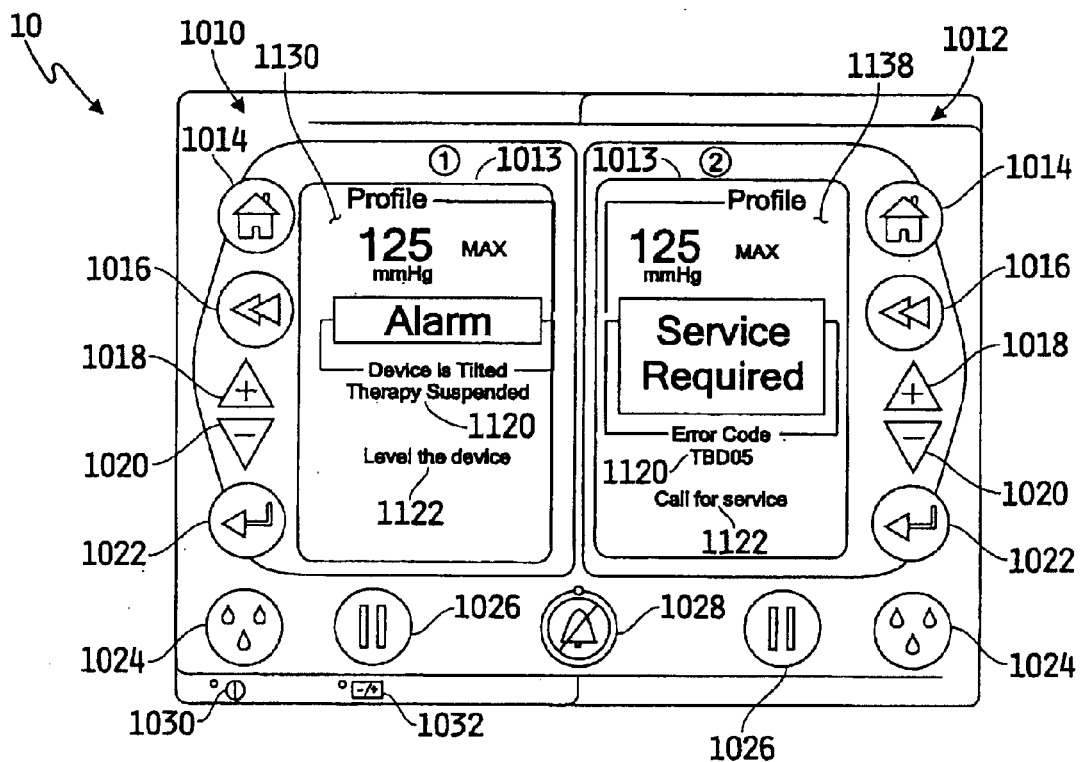
Figure 47:
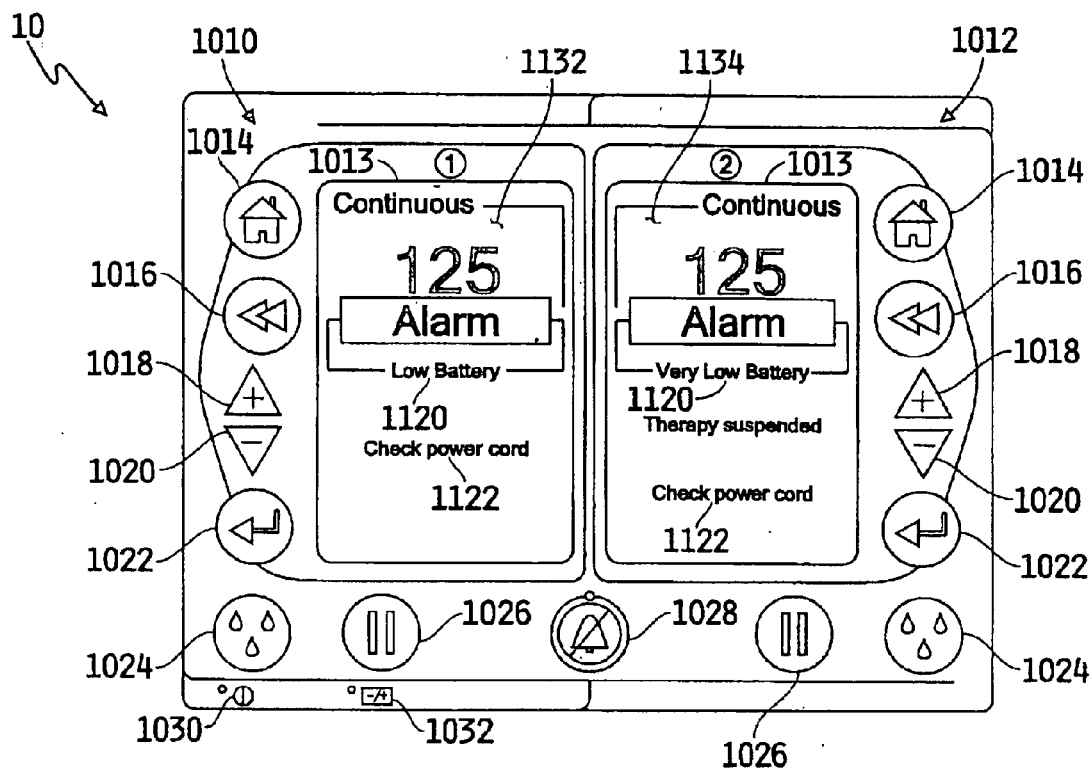
Figure 48:
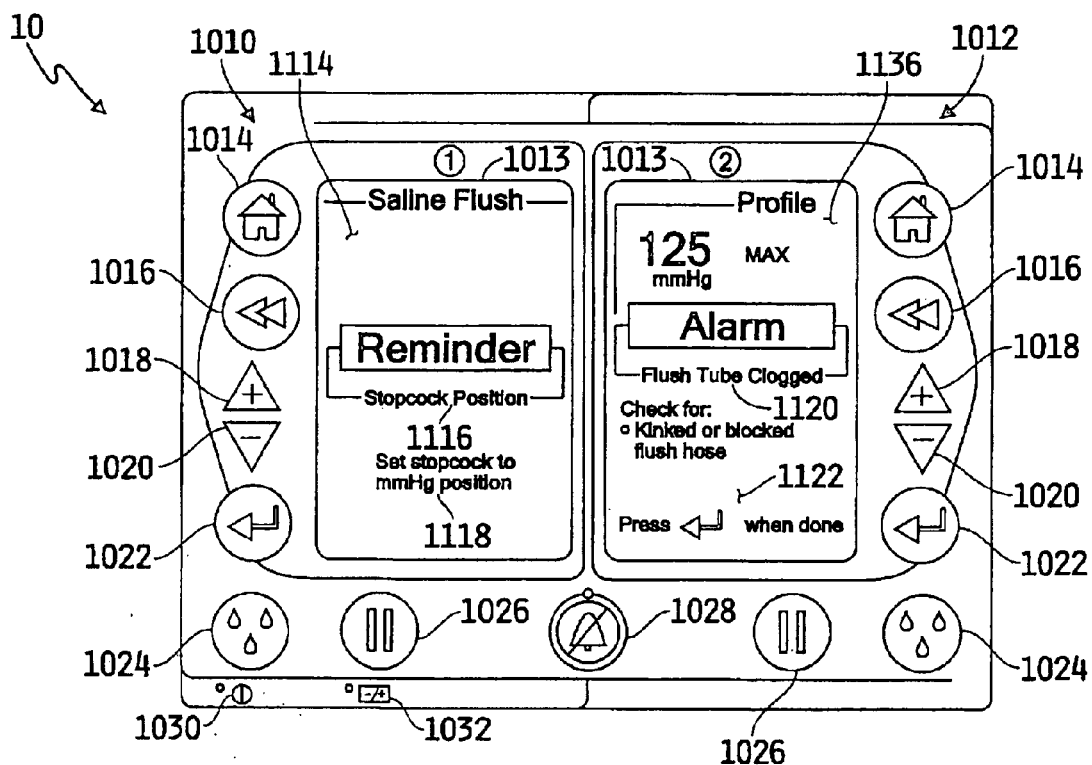

Alarm activations from Reminder conditions are shown in FIGS. 43, 44, and 48. Conditions that result in such alarm activations include pressing irrigation button 1024 when the respective syringe 24 is empty (see screen 1109 in FIG. 43), pressing irrigation button 1024 when the respective door 832 is open (see screen 1111 in FIG. 43), activating the Continuous or Profile mode when the respective waste collection canister 826 is not positioned within its receptacle 840 (see screen 1112 in FIG. 44), and when the flush menu is exited (see screen 1114 in FIG. 48).

In each of screens 1109, 1111, 1112, 1114, the text "Reminder" appears and information 1116, 1118 is displayed informing the user of the condition and how to troubleshoot the condition. In screen 1109, information 1116 informs the user that the respective syringe 24 is empty and information 1118 instructs the user to install another syringe 24. In screen 1111, information 1116 informs the user that the respective door 832 is open and information 1118 instructs the user to shut the door 832. In screen 1112, information 1116 informs the user that the respective canister 826 is missing and information 1118 instructs the user to install the canister 826. In screen 1114, information 1116 informs the user that the position of stopcock 1101 is incorrect and information 1118 instructs the user to set stopcock 1101 to its vacuum position.

When an alarm activation due to a Reminder condition occurs, the respective screen 1109, 1111, 1112, 1114 appears on the respective display 1013 for a predetermined period of time, such as five seconds, and audible alarm 868 is activated for another predetermined period of time, such as one second. The screen then disappears and the respective system 806, 808 continues in its previous mode.

A screen with the word "Alarm" appears on the respective display 1013 and audible alarm 868 activates when an Alarm condition occurs, as shown in FIGS. 42 and 44–48. Information 1120, 1122 is provided on the respective screen to indicate the condition and how to troubleshoot the condition.

Examples of Alarm conditions are shown in FIGS. 42 and 44–48. A screen 1124 (see FIG. 42) provides information 1120 to alert the user that one of the flush screens 1100, 1106 has been inactive for a predetermined period of time, such as one minute, and information 1122 to instruct the user how to remedy that condition. A screen 1123 (see FIG. 44) provides information 1120 to alert the user that one of waste collection canisters 826 is removed from its respective receptacle 840 during operation of the respective vacuum source 110 and information 1122 to instruct the user to install the removed canister 826 and press enter button 1022 when installation is complete.

A screen 1126 (see FIG. 45) provides information 1120 to alert the user of an occluded system and information 1122 to instruct the user to check for a kinked or blocked hose and to check whether stopcock 1101 is in its flush position and then press enter button 1022 when finished unkinking or unblocking the hose or moving stopcock 1101 to its vacuum position.

A screen 1128 (see FIG. 45) provides information 1120 to alert the user that vacuum wound therapy has stopped and information 1122 to instruct the user to check for a full waste collection canister 826, loose film dressing, or improper hose connection and then press enter button 1022 when finished correcting the condition that caused the alarm.

A screen 1130 (see FIG. 46) provides information 1120 to alert the user that control unit 803 is tilted beyond forty-five degrees thereby causing wound therapy to be suspended and information 1122 to instruct the user to level control unit 803. A screen 1132 (see FIG. 47) provides information 1120 to alert the user that battery 954 is nearing the end of its electrical charge (e.g., battery 954 has about fifteen minutes of electrical charge remaining) and information 1122 to instruct the user to check the power cord of control unit 803. A screen 1134 (see FIG. 47) provides information 1120 to alert the user that battery 954 will soon (e.g., in about two minutes) reach the end of its electrical charge and information 1122 to instruct the user to again check the power cord of control unit 803 and to advise the user that therapy is suspended. When screen 1134 appears, the respective alarm 868 will sound continuously until the power cord is plugged into an electrical power outlet and control unit 803 will stop providing vacuum therapy.

A screen 1136 (see FIG. 48) provides information 1120 to alert the user if plunger interface 78 does not reach full travel within a predetermined period of time (e.g., within fifteen seconds) and information 1122 to instruct the user to check whether hose 18 is blocked or kinked and then to press enter button 1022 when finished unkinking or unblocking the hose. Plunger interface 78 may also fail to reach full travel within the predetermined period of time because stopcock 1101 is in its vacuum position instead of its flush position.

The user presses enter button 1022 after taking corrective measures to address the Alarm condition. If the Alarm condition has been corrected, no alarm 868 will sound, the respective screen 1123, 1124, 1126, 1128, 1130, 1132, 1134, 1136 will disappear from the respective display 1013, and vacuum therapy will resume.

On the other hand, if the Alarm condition has not been corrected, pressing enter button 1022 will silence and reset the respective alarm 868. However, the respective system 806, 808 will redetect the Alarm condition and upon detection thereof the respective alarm 868 will activate again and the respective screen 1123, 1124, 1126, 1128, 1130, 1132, 1134, 1136 will reappear.

A Service Required screen 1138 (see FIG. 46) with the words "Service Required" appears on the respective display 1013 when the respective system 806, 808 needs to be serviced. Screen 1138 provides information 1120 which provides an error code and information 1122 to instruct a user to call a service technician to address the problem associated with the error code. Audible alarm 868 is activated when screen 1138 appears. It is intended that, in the event of a Service Required condition, a service technician would provide the necessary service for the respective system 806, 808 and clear the alarm 868 caused by the Service Required condition.

Although the foregoing apparatus has been described, one skilled in the art can easily ascertain the essential characteristics of the apparatus, and various changes and modifications may be made to adapt the various uses and characteristics without departing from the spirit and scope of this disclosure, as described by the claims which follow.

What is claimed is:

1. A method for calibrating a control unit adapted to provide a negative pressure through a vacuum wound bandage associated with a wound of a patient, the method comprising
   positioning a first pressure sensor in communication with the control unit,
   correlating a first output of a second pressure sensor of the control unit to a first calibration pressure when the first pressure sensor senses the first calibration pressure, and
   correlating a second output of the second pressure sensor to a second calibration pressure when the second pressure sensor senses the second calibration pressure.

2. The method of claim 1, wherein positioning a first pressure sensor in communication with the control unit includes positioning the first pressure sensor in communication with a waste collection canister that is configured to collect waste material from the vacuum wound bandage and communicates with the second pressure sensor.

3. The method of claim 2, wherein positioning the first pressure sensor in communication with a waste collection canister that is configured to collect waste material from the vacuum wound bandage and communicates with the second pressure sensor includes positioning the first pressure sensor in communication with a port configured to receive waste material from the vacuum wound bandage.

4. The method of claim 2, wherein correlating a first output of a second pressure sensor of the control unit to a first calibration pressure when the first pressure sensor senses the first calibration pressure includes establishing atmospheric pressure, which is the first calibration pressure, in the waste collection canister to cause the first pressure sensor and the second pressure sensor to communicate with atmospheric pressure.

5. The method of claim 4, wherein establishing atmospheric pressure in the waste collection canister to cause the first pressure sensor and the second pressure sensor to communicate with atmospheric pressure includes blocking communication between the waste collection canister and a vacuum source.

6. The method of claim 5, wherein blocking communication between the waste collection canister and a vacuum source includes closing a valve between the waste collection canister and the vacuum source.

7. The method of claim 4, wherein correlating a first output of a second pressure sensor of the control unit to a first calibration pressure when the first pressure sensor senses the first calibration pressure includes observing that the first pressure sensor indicates that atmospheric pressure has been established in the waste collection canister.

8. The method of claim 4, wherein correlating a first output of a second pressure sensor of the control unit to a first calibration pressure when the first pressure sensor senses the first calibration pressure includes storing the first output when the first pressure sensor indicates that atmospheric pressure has been established in the waste collection canister.

9. The method of claim 8, wherein storing the first output when the first pressure sensor indicates that atmospheric pressure has been established in the waste collection canister includes operating a user control.

10. The method of claim 2, wherein correlating a second output of the second pressure sensor to a second calibration pressure when the second pressure sensor senses the second calibration pressure includes establishing the second calibration pressure, which is less than atmospheric pressure, in the waste collection canister to cause the first pressure sensor and the second pressure sensor to communicate with the second calibration pressure.

11. The method of claim 10, wherein establishing the second calibration pressure, which is less than atmospheric pressure, in the waste collection canister to cause the first pressure sensor and the second pressure sensor to communicate with the second calibration pressure includes moving a valve to permit communication between the waste collection canister and a vacuum source.

12. The method of claim 10, wherein establishing the second calibration pressure in the waste collection canister to cause the first pressure sensor and the second pressure sensor to communicate with the second calibration pressure includes operating a user control.

13. The method of claim 1, wherein correlating a second output of the second pressure sensor to a second calibration pressure when the second pressure sensor senses the second calibration pressure includes operating a vacuum source of the control unit to provide the second calibration pressure.

14. The method of claim 1, wherein correlating a first output of a second pressure sensor of the control unit to a first calibration pressure when the first pressure sensor senses the first calibration pressure includes storing the first output when the first pressure sensor senses the first calibration pressure.

15. The method of claim 14, wherein correlating a second output of the second pressure sensor to a second calibration pressure when the second pressure sensor senses the second calibration pressure includes storing the second output when the first pressure sensor senses the second calibration pressure.

16. The method of claim 1, further comprising displaying calibration information on a display of the control unit.

17. The method of claim 1, wherein positioning a first pressure sensor in communication with the control unit includes positioning a manometer in communication with the control unit.

* * * * *